(12) United States Patent
Wolf et al.

(10) Patent No.: US 7,148,382 B2
(45) Date of Patent: Dec. 12, 2006

(54) BATHOCHROMIC MONO- AND BIS-ACYLPHOSPHINE OXIDES AND SULFIDES AND THEIR USE AS PHOTOINITIATORS

(75) Inventors: Jean-Pierre Wolf, Maisprach (CH); Gebhard Hug, Rheinfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 153 days.

(21) Appl. No.: 10/485,836

(22) PCT Filed: Aug. 13, 2002

(86) PCT No.: PCT/EP02/09045

§ 371 (c)(1),
(2), (4) Date: Feb. 4, 2004

(87) PCT Pub. No.: WO03/019295

PCT Pub. Date: Mar. 6, 2003

(65) Prior Publication Data

US 2004/0204613 A1 Oct. 14, 2004

(30) Foreign Application Priority Data

Aug. 21, 2001 (CH) ..................... 1542/01

(51) Int. Cl.
C07F 9/02 (2006.01)
(52) U.S. Cl. .................. 568/14; 564/15; 558/153
(58) Field of Classification Search ............... 558/153; 568/14; 564/15
See application file for complete search history.

(56) References Cited

U.S. PATENT DOCUMENTS

| 4,292,152 | A | 9/1981 | Lechtken et al. | 204/159.15 |
| 4,737,593 | A | 4/1988 | Ellrich et al. | 568/15 |
| 5,498,741 | A * | 3/1996 | Kleiner | 558/118 |
| 6,284,813 | B1 | 9/2001 | Leppard et al. | 522/8 |
| 6,399,805 | B1 | 6/2002 | Wolf et al. | 556/405 |
| 6,737,549 | B1 | 5/2004 | Wolf et al. | 568/14 |
| 2003/0164580 | A1 | 9/2003 | Rinker et al. | 264/496 |

FOREIGN PATENT DOCUMENTS

| CH | 691970 | 12/2001 |
| DE | 3139984 | 4/1983 |
| EP | 0495752 | 7/1992 |
| EP | 0600373 | 6/1994 |
| GB | 2365430 | 2/2002 |
| JP | 10-279787 | * 10/1998 |
| WO | 0032612 | 6/2000 |

OTHER PUBLICATIONS

Derwent Abstract 92-243583/30 for EP 495752 (1992).
Derwent Abstract 41862 for DE 3139984 (1983).
2244 Research Disclosure, Jun. 1993, No. 350, pp. 414-416.

* cited by examiner

Primary Examiner—Thurman K. Page
Assistant Examiner—Chukwuma Nwaonicha
(74) Attorney, Agent, or Firm—Joseph C. Suhadolnik

(57) ABSTRACT

Compounds of formula (I), wherein A is S or O; x is 0 or 1; a is $SR_{10}$ or $N(R_{11})(R_{12})$; $R_1$ and $R_2$ are $C_1$–$C_{24}$alkyl, $OR_{10}$, $CF_3$ or halogen; $R_3$, $R_4$ and $R_5$ are hydrogen, $C_1$–$C_{24}$alkyl, $OR_{10}$ or halogen; or two of the radicals $R_{11}$ $R_{21}$ $R_{31}$ $R_4$ and/or $R_9$ together form $C_1$–$C_{20}$alkylene uninterrupted or interrupted by O, S or $NR_{13}$; $R_6$, $R_{11}$ $R_8$ and $R_9$ are hydrogen, $C_1$–$C_{24}$alkyl; $C_2$–$C_{24}$alkyl which is interrupted one or more times by non-consecutive O atoms and unsubstituted or substituted by OH and/or SH, or $R_6$, $R_7$, $R_8$ and Rg are $OR_{10}$; halogen; or phenyl unsubstituted or substituted one or more times by C-Calkyl; $R_{10}$, $R_{11}$ and $R_{12}$ are e.g. hydrogen; X is e.g. (II), and $R_2$; have one of the meanings given for $R_1$ and $R_2$; and $R_3$', $R_4$' and Rs' have one of the meanings given for $R_3$, $R_4$ and $R_5$; are suitable as photoinitiators, especially for irradiation with light of relatively long wavelengths

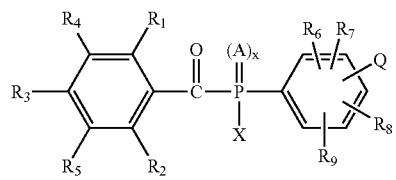

(I)

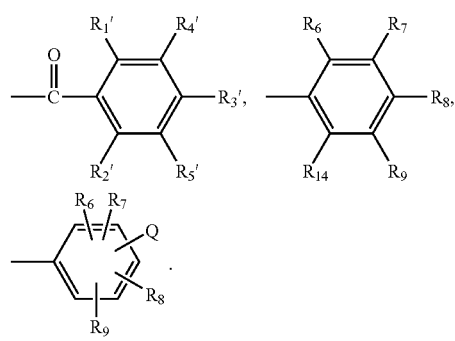

(II)

8 Claims, No Drawings

BATHOCHROMIC MONO- AND BIS-ACYLPHOSPHINE OXIDES AND SULFIDES AND THEIR USE AS PHOTOINITIATORS

The present application relates to bathochromic mono- and bis-acylphosphine oxides and sulfides, to starting materials for the preparation of those compounds, and to the preparation and use of the compounds as photoinitiators.

The use of mono- and bis-acylphosphine oxides and sulfides as photoinitiators is known and is published, for example, in U.S. Pat. Nos. 4,292,152, U.S. 4,737,593 and EP 495 752.

U.S. Pat. No. 6,399,805 and GB 2 365 430 describe selective processes for the preparation of asymmetric mono- and bis-acylphosphine oxides and sulfides, and the synthesis of the starting materials used in that process.

In the art, readily available starting materials for the preparation of acylphosphine oxides and sulfides are of great importance. Of particular interest are compounds that are active when irradiated with light of relatively long wavelength, that is to say that absorb light of that wavelength.

It has now been found that the above-mentioned preparation processes offer access to novel bathochromic mono- and bis-acylphosphine oxide and sulfide photoiniators.

The invention accordingly relates to compounds of formula I

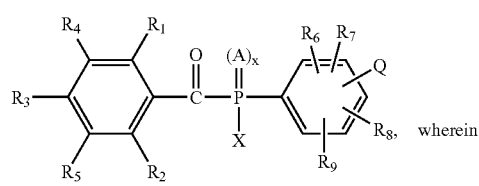

wherein

A is S or O;
x is 0 or 1;
Q is $SR_{10}$ or $N(R_{11})(R_{12})$;
$R_1$ and $R_2$ are each independently of the other $C_1$–$C_{24}$alkyl, $OR_{10}$, $CF_3$ or halogen;
$R_3$, $R_4$ and $R_5$ are each independently of the others hydrogen, $C_1$–$C_{24}$alkyl, $OR_{10}$ or halogen; or two of the radicals $R_1$, $R_2$, $R_3$, $R_4$ and/or $R_5$ together form $C_1$–$C_{20}$alkylene which is uninterrupted or interrupted by O, S or $NR_{13}$;
$R_6$, $R_7$, $R_8$ and $R_9$ are each independently of the others hydrogen, $C_1$–$C_{24}$alkyl; $C_2$–$C_{24}$alkyl which is interrupted one or more times by non-consecutive O atoms and which is unsubstituted or substituted by OH and/or SH; or $R_6$, $R_7$, $R_8$ and $R_9$ are $OR_{10}$; halogen; or phenyl unsubstituted or substituted one or more times by $C_1$–$C_4$alkyl;
$R_{10}$, $R_{11}$ and $R_{12}$ are each independently of the others hydrogen, $C_1$–$C_{24}$alkyl, $C_2$–$C_{24}$alkenyl, $C_3$–$C_8$cycloalkyl, phenyl, benzyl, or $C_2$–$C_{20}$alkyl which is interrupted one or more times by non-consecutive O atoms and which is unsubstituted or substituted by OH and/or SH; or
$R_{11}$ and $R_{12}$ together with the N atom to which they are bonded form a 5 or 6-membered ring, which may also contain O or S atoms or an $NR_{13}$ group;
$R_{13}$ is hydrogen, phenyl, $C_1$–$C_{12}$alkoxy, $C_1$–$C_{12}$alkyl, or $C_2$–$C_{12}$alkyl which is interrupted one or more times by O or S and which is unsubstituted or substituted by OH and/or SH;

X is

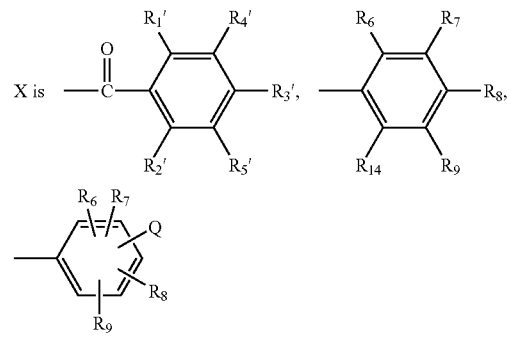

or $OR_{10}$ or X is $C_1$–$C_{24}$alkyl which is unsubstituted or substituted one or more times by $OR_{15}$, $SR_{15}$, $N(R_{16})(R_{17})$, phenyl, halogen, CN, —N=C=A,

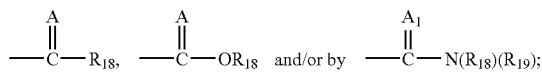

or X is $C_2$–$C_{24}$alkyl which is interrupted one or more times by O, S or $NR_{13}$ and which is unsubstituted or substituted by $OR_{15}$, $SR_{15}$, $N(R_{16})(R_{17})$, phenyl, halogen,

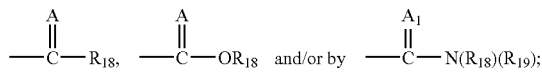

or X is $C_1$–$C_{24}$alkoxy which is uninterrupted or interrupted one or more times by O, S or $NR_{13}$ and which is unsubstituted or substituted one or more times by $OR_{15}$, $SR_{15}$, $N(R_{16})(R_{17})$, phenyl, CN,

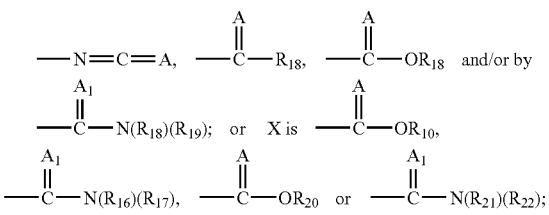

or X is $C_3$–$C_{24}$cycloalkyl unsubstituted or substituted by $C_1$–$C_{20}$alkyl, $OR_{10}$, $CF_3$ or by halogen; or $C_2$–$C_{24}$alkenyl unsubstituted or substituted by $C_6$–$C_{14}$aryl, CN, (CO)$OR_{15}$ or by (CO)$N(R_{18})(R_{19})$;

or X is $C_3$–$C_{24}$cycloalkenyl or is one of the radicals (a)

$$\begin{array}{c} R_{27} \quad R_{26} \\ \text{—}X_1\text{—}\phantom{xx}\text{—}R_{25}, \\ R_{23} \quad R_{24} \end{array}$$

-continued (b) 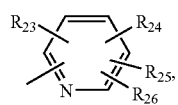

(c) 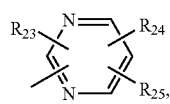

(d) 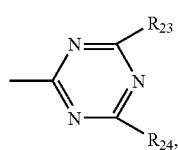

(e) 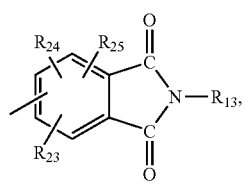

(f) 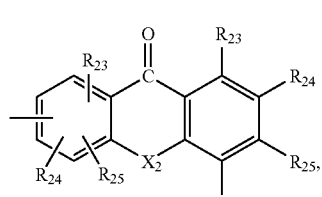

(g) 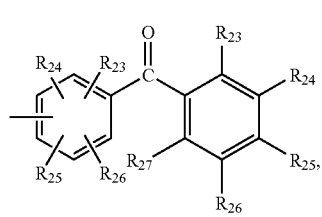

(h) 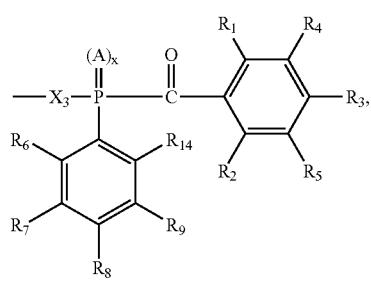

(i) 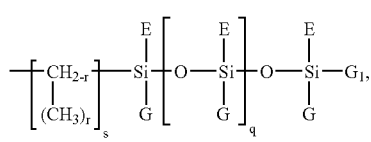

(k) 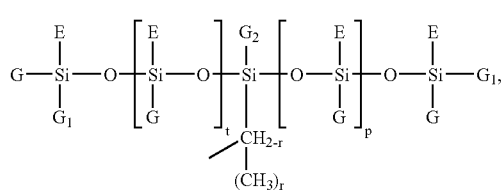

-continued (m) 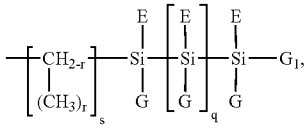

(n) 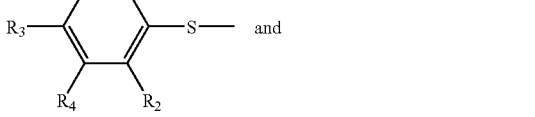

(o) 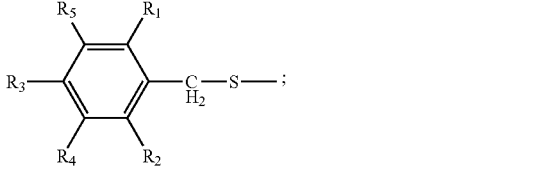

or X is $C_1$–$C_{24}$alkylthio wherein the alkyl radical is uninterrupted or interrupted one or more times by non-consecutive O or S and unsubstituted or substituted by $OR_{15}$, $SR_{15}$ and/or halogen;

$A_1$ is O, S or $NR_{21}$;

$R_{14}$ has one of the meanings given for $R_6$, $R_7$, $R_8$ and $R_9$;

$R_1'$ and $R_2'$ each independently of the other has one of the meanings given for $R_1$ and $R_2$;

$R_3'$, $R_4'$ and $R_5'$ each independently of the others has one of the meanings given for $R_3$, $R_4$ and $R_5$;

$R_{15}$, $R_{16}$ and $R_{17}$ each independently of the others has one of the meanings given for $R_{10}$ or is a radical

$R_{18}$ and $R_{19}$ are each independently of the other hydrogen, $C_1$–$C_{24}$alkyl, $C_2$–$C_{12}$alkenyl, $C_3$–$C_8$-cycloalkyl, phenyl, benzyl; or $C_2$–$C_{20}$alkyl which is interrupted one or more times by O or S and which is unsubstituted or substituted by OH;

$R_{20}$ is $C_1$–$C_{20}$alkyl which is substituted one or more times by $OR_{15}$ or halogen; or is $C_2$–$C_{20}$-alkyl which is interrupted one or more times by non-consecutive O atoms and which is unsubstituted or substituted one or more times by $OR_{15}$ or halogen; or $R_{20}$ is $C_2$–$C_{20}$alkenyl or $C_2$–$C_{12}$alkynyl; or $R_{20}$ is $C_3$–$C_{12}$cycloalkenyl which is substituted one or more times by halogen, $NO_2$, $C_1$–$C_6$alkyl, $OR_{10}$ or by $C(O)OR_{18}$; or is $C_7$–$C_{16}$arylalkyl or $C_8$–$C_{16}$arylcycloalkyl;

$R_{21}$ and $R_{22}$ are each independently of the other hydrogen; $C_1$–$C_{20}$alkyl which is substituted one or more times by $OR_{15}$, halogen, styryl, methylstyryl or by —N=C=A; or $C_2$–$C_{20}$alkyl which is interrupted one or more times by non-consecutive O atoms and which is unsubstituted or substituted one or more times by $OR_{15}$, halogen, styryl or by methylstyryl; or $R_{21}$ and $R_{22}$ are each independently of the other $C_2$–$C_{12}$alkenyl; $C_5$–$C_{12}$cycloalkyl which is substituted by —N=C=A or —$CH_2$—N=C=A and may additionally be substituted by one or more $C_1$–$C_4$alkyl substituents; or $R_{21}$ and $R_{22}$ are each independently of the other $C_6$–$C_{14}$aryl unsubstituted or substituted one or more times by halogen, $NO_2$, $C_1$–$C_6$alkyl, $C_2$–$C_4$alkenyl, $OR_{10}$, —N═C═A, —$CH_2$—N═C═A or by $C(O)OR_{18}$; or $R_{21}$ and $R_{22}$ are $C_7$–$C_{16}$arylalkyl; or $R_{21}$ and $R_{22}$ together are $C_8$–$C_{16}$arylcycloalkyl; or $R_{21}$ and $R_{22}$ are each independently of the other

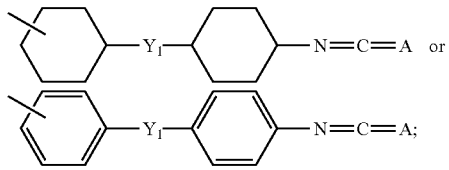

$Y_1$ is O, S, SO, $SO_2$, $CH_2$, $C(CH_3)_2$, $CHCH_3$, $C(CF_3)_2$, (CO) or a direct bond;

$R_{23}$, $R_{24}$, $R_{25}$, $R_{26}$ and $R_{27}$ have one of the meanings given for $R_6$ or are $NO_2$, CN, $SO_2R_{28}$, $OSO_2R_{24}$, $CF_3$, $CCl_3$ or halogen;

$R_{28}$ is $C_1$–$C_{12}$alkyl, halo-substituted $C_1$–$C_{12}$alkyl, phenyl, or phenyl substituted by $OR_{15}$ and/or $SR_{15}$;

$X_1$ is $CH_2$, $CHCH_3$ or $C(CH_3)_2$;

$X_2$ is S, O, $CH_2$, C═O, $NR_{13}$ or a direct bond;

$X_3$ is $C_1$–$C_{24}$alkylene; $C_2$–$C_{24}$alkylene interrupted one or more times by O, S or $NR_{13}$;

$C_2$–$C_{24}$alkenylene; $C_2$–$C_{24}$alkenylene interrupted one or more times by O, S or $NR_{13}$;

$C_3$–$C_{24}$cycloalkylene; $C_3$–$C_{24}$cycloalkylene interrupted one or more times by O, S or $NR_{13}$;

$C_3$–$C_{24}$cycloalkenylene; or $C_3$–$C_{24}$cycloalkenylene interrupted one or more times by O, S or $NR_{13}$;

the radicals $C_1$–$C_{24}$alkylene, $C_2$–$C_{24}$alkylene, $C_2$–$C_{24}$alkenylene, $C_3$–$C_{24}$cycloalkylene and $C_3$–$C_{24}$cycloalkenylene being unsubstituted or substituted by $OR_{10}$, $SR_{10}$, $N(R_{11})(R_{12})$ and/or by halogen; or $X_3$ is one of the radicals phenylene,

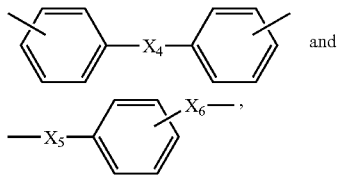

those radicals being unsubstituted or substituted on the aromatic ring by $C_1$–$C_{20}$alkyl; $C_2$–$C_{20}$alkyl which is interrupted one or more times by non-consecutive O atoms and which is unsubstituted or substituted by OH and/or SH; $OR_{10}$, $SR_{10}$, $N(R_{11})(R_{12})$, phenyl, halogen, $NO_2$, CN, (CO)—$OR_{18}$, (CO)—$R_{18}$, (CO)—$N(R_{18})(R_{19})$, $SO_2R_{28}$, $OSO_2R_{28}$, $CF_3$ and/or by $CCl_3$;

or $X_3$ is a group

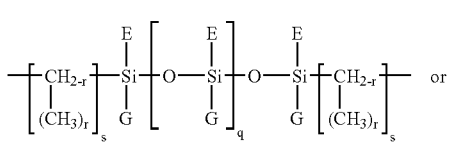

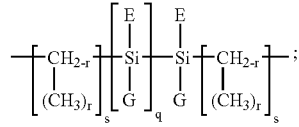

$X_4$ is S, O, $CH_2$, $CHCH_3$, $C(CH_3)_2$, $C(CF_3)_2$, CO, SO or $SO_2$;

$X_5$ and $X_6$ are each independently of the other $CH_2$, $CHCH_3$ or $C(CH_3)_2$;

r is 0, 1 or 2;

s is a number from 1 to 12;

q is a number from 0 to 50;

t and p are each a number from 0 to 20; and

E, G, $G_1$ and $G_2$ are each independently of the others unsubstituted or halo-substituted $C_1$–$C_{12}$alkyl, or phenyl unsubstituted or substituted by one or more $C_1$–$C_4$alkyl substituents.

$C_1$–$C_{24}$Alkyl is linear or branched and is, for example, $C_2$–$C_{24}$-, $C_1$–$C_{20}$-, $C_1$–$C_{18}$-, $C_1$–$C_{12}$-, $C_1$–$C_8$-, $C_1$–$C_6$- or $C_1$–$C_4$-alkyl. Examples are methyl, ethyl, propyl, isopropyl, n-butyl, sec-butyl, isobutyl, tert-butyl, pentyl, hexyl, heptyl, 2,4,4-trimethyl-pentyl, 2-ethylhexyl, octyl, nonyl, decyl, undecyl, dodecyl, tetradecyl, pentadecyl, hexadecyl, heptadecyl, octadecyl, nonadecyl, icosyl and tetraicosyl.

For example, $R_1$, $R_2$, $R_3$, $R_4$, $R_5$, $R_6$, $R_7$, $R_8$ and $R_9$ and also $R_1'$, $R_2'$, $R_3'$, $R_4'$ and $R_5'$ as alkyl are $C_1$–$C_8$alkyl, especially $C_1$–$C_6$alkyl, preferably $C_1$–$C_4$alkyl, more especially methyl.

$C_1$–$C_{20}$-, $C_1$–$C_{18}$-, $C_1$–$C_{12}$-, $C_1$–$C_6$ and $C_1$–$C_4$-alkyl are likewise linear or branched and have e.g. the meanings given above up to the appropriate number of carbon atoms.

$C_2$–$C_{24}$Alkyl that is interrupted one or more times by O, S or $NR_{13}$ is, for example, interrupted from 1 to 9 times, e.g. from 1 to 7 times or once or twice, by O, S or $NR_{13}$. When the radicals are interrupted by a plurality of O, S or $NR_{13}$, the O atoms, S atoms or $NR_{13}$ groups, as the case may be, are separated from one another by at least one methylene group. The O atoms, S atoms or $NR_{13}$ groups therefore are not directly consecutive. The alkyl radical may be linear or branched. There are thus obtained e.g. structural units such as —$CH_2$—O—$CH_3$, —$CH_2CH_2$—O—$CH_2CH_3$, —[$CH_2CH_2O$]$_z$—$CH_3$ wherein z=1 to 9, —($CH_2CH_2O$)$_7$ $CH_2CH_3$, —$CH_2$—$CH(CH_3)$—O—$CH_2$—$CH_2CH_3$, —$CH_2$—$CH(CH_3)$—O—$CH_2$—$CH_3$, —$CH_2SCH_3$ and $CH_2$—$N(CH_3)_2$.

$C_2$–$C_{20}$-, $C_2$–$C_{18}$ and $C_2$–$C_{12}$-alkyl that are interrupted by O and possibly by S are likewise linear or branched and can have, for example, the meanings given above up to the number of carbon atoms indicated. In this case too the O atoms are not consecutive.

$C_3$–$C_{24}$Cycloalkyl, e.g. $C_5$–$C_{12}$-, $C_3$–$C_{12}$- or $C_3$–$C_8$-cycloalkyl, denotes both single and bridged alkyl ring systems. In addition, the radicals may also contain linear or branched alkyl groups (as described above up to the appropriate number of carbon atoms). Examples are e.g. cyclopropyl, cyclopentyl, cyclohexyl, cyclooctyl, cyclododecyl, cycloicosyl, adamantyl, especially cyclopentyl and cyclohexyl, preferably cyclohexyl. Further examples are

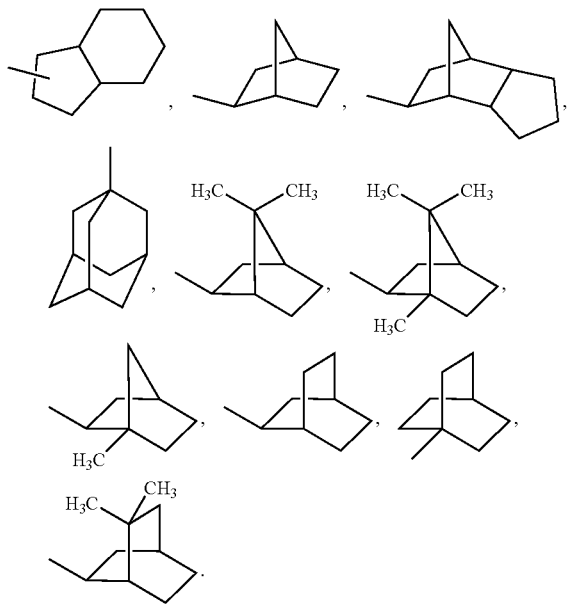

$C_3$–$C_8$Cycloalkyl, e.g. $C_3$–$C_6$cycloalkyl, can have the meanings given above up to the appropriate number of carbon atoms.

$C_3$–$C_{24}$Cycloalkyl substituted by $C_1$–$C_{20}$alkyl, $OR_{10}$, $CF_3$ or halogen is preferably tri- or di-substituted in the 2,4,6- or 2,6-positions of the cycloalkyl ring. 2,4,6-Trimethylcyclohexyl and 2,6-dimethoxycyclohexyl are preferred.

$C_2$–$C_{24}$Alkenyl radicals are mono- or poly-unsaturated and also linear or branched and are, for example, $C_2$–$C_{18}$-, $C_2$–$C_8$-, $C_2$–$C_6$- or $C_2$–$C_4$-alkenyl. Examples are vinyl, allyl, methallyl, 1,1-dimethylallyl, 1-butenyl, 2-butenyl, 1,3-pentadienyl, 1-hexenyl, 1-octenyl, decenyl and dodecenyl, especially allyl. $C_2$–$C_{18}$Alkenyl is as defined above up to the appropriate number of carbon atoms.

When $C_2$–$C_{24}$alkenyl radicals are interrupted e.g. by O, the following structures, for example, are included: —$(CH_2)_y$—O—$(CH_2)_x$—CH=$CH_2$, —$(CH_2)_y$—O—$(CH_2)_x$—C($CH_3$)=$CH_2$ and —$(CH_2)_y$—O—CH=$CH_2$ wherein x and y are each independently of the other a number from 1 to 21.

$C_3$–$C_{24}$Cycloalkenyl, e.g. $C_5$–$C_{12}$-, $C_3$–$C_{12}$- or $C_3$–$C_8$-cycloalkenyl, denotes both single and bridged alkyl ring systems and may be mono- or poly-unsaturated, e.g. mono- or di-unsaturated. In addition, the radicals may also contain linear or branched alkyl groups (as described above up to the appropriate number of carbon atoms). Examples are e.g. cyclopropenyl, cyclopentenyl, cyclohexenyl, cyclooctenyl, cyclododecenyl, cycloicosenyl, especially cyclopentenyl and cyclohexenyl, preferably cyclohexenyl.

$C_2$–$C_{12}$Alkynyl is mono- or poly-unsaturated, linear or branched and is e.g. $C_2$–$C_8$-, $C_2$–$C_6$- or $C_2$–$C_4$-alkynyl. Examples are ethynyl, propynyl, butynyl, 1-butynyl, 3-butynyl, 2-butynyl, pentynyl, hexynyl, 2-hexynyl, 5-hexynyl, octynyl, etc.

$C_6$–$C_{14}$Aryl is, for example, $C_6$–$C_{12}$- or $C_6$–$C_{10}$-aryl. Examples are phenyl, naphthyl, biphenylyl, anthracyl and phenanthryl, preferably phenyl or naphthyl, especially phenyl.

$C_7$–$C_{16}$Arylalkyl is, for example, $C_7$–$C_{11}$arylalkyl. The alkyl radical in that group may be either linear or branched. Examples are benzyl, phenylethyl, α-methylbenzyl, phenylpentyl, phenylhexyl, α,α-dimethylbenzyl and naphthylmethyl, especially benzyl. Substituted $C_7$–$C_{11}$arylalkyl is mono- to tetra-substituted, e.g. mono-, di- or tri-substituted, especially mono- or di-substituted, at the aryl ring.

$C_8$–$C_{16}$Arylcycloalkyl is e.g. $C_9$–$C_{16}$- or $C_9$–$C_{13}$-arylcycloalkyl and denotes cycloalkyl that is fused to one or more aryl rings. Examples are

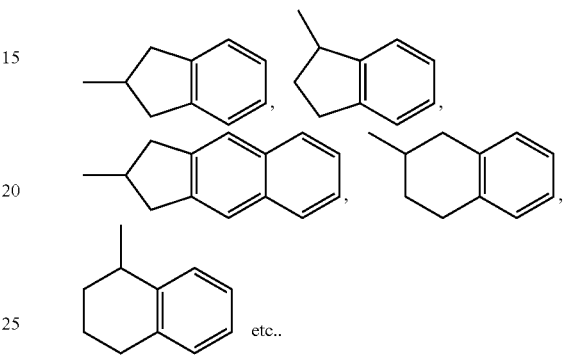

etc..

$C_1$–$C_{12}$Alkoxy denotes linear or branched radicals and is, for example, $C_1$–$C_{10}$-, $C_1$–$C_8$-, $C_1$–$C_6$- or $C_1$–$C_4$-alkoxy. Examples are methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy and dodecyloxy, especially methoxy, ethoxy, propoxy, isopropoxy, n-butyloxy, sec-butyloxy, isobutyloxy and tert-butyloxy, preferably methoxy.

$C_1$–$C_{24}$Alkylthio denotes linear or branched radicals and is, for example, $C_1$–$C_{12}$-, $C_1$–$C_{10}$-, $C_1$–$C_8$-, $C_1$–$C_6$- or $C_1$–$C_4$-alkylthio. Examples are methylthio, ethylthio, propylthio, isopropylthio, n-butylthio, sec-butylthio, isobutylthio, tert-butylthio, pentylthio, hexylthio, heptylthio, 2,4,4-trimethylpentylthio, 2-ethylhexylthio, octylthio, nonylthio, decylthio, dodecylthio, icosylthio, especially methylthio, ethylthio, propylthio, isopropylthio, n-butylthio, sec-butylthio, isobutylthio and tert-butylthio, preferably methylthio.

$C_1$–$C_8$Alkylthio is likewise linear or branched and is, for example, as defined above up to the appropriate number of carbon atoms.

$C_1$–$C_{24}$Alkylene is linear or branched and is e.g. $C_1$–$C_{20}$-, $C_1$–$C_{12}$-, $C_1$–$C_8$-, or $C_2$–$C_8$- or $C_1$–$C_4$-alkylene, such as methylene, ethylene, propylene, isopropylene, n-butylene, sec-butylene, isobutylene, tert-butylene, pentylene, hexylene, heptylene, octylene, nonylene, decylene, dodecylene, tetradecylene, heptadecylene, octadecylene, icosylene or e.g. $C_1$–$C_{12}$alkylene, such as ethylene, decylene,

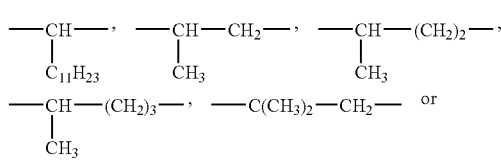

-continued

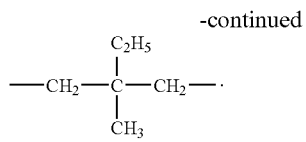

$C_2-C_{18}$Alkylene is also linear or branched, e.g. $C_2-C_8$- or $C_2-C_4$-alkylene, and is as defined above up to the appropriate number of carbon atoms.

When $C_2-C_{24}$alkylene is interrupted one or more times by O, S or $NR_{13}$, it is interrupted, for example, from 1 to 9 times, e.g. from 1 to 7 times or once or twice, by O, S or $NR_{13}$, thus yielding e.g. structural units such as $-CH_2-O-CH_2-$, $-CH_2CH_2-O-CH_2CH_2-$, $-[CH_2CH_2-O]_z-$ wherein z=1 to 9, $-(CH_2CH_2O)_7CH_2CH_2-$, $-CH_2-CH(CH_3)-O-CH_2-CH(CH_3)-$, $-CH_2-S-CH_2-$, $-CH_2CH_2-S-CH_2CH_2-$, $-CH_2CH_2CH_2-S-CH_2CH_2CH_2-$, $-(CH_2)_3-S-(CH_2)_3-S-(CH_2)_3-$, $-CH_2-(NR_{13})-CH_2-$ and $-CH_2CH_2-(NR_{13})-CH_2CH_2-$. The alkylene radicals may be linear or branched and, when the alkylene radicals are interrupted by a plurality of O, S or $NR_{13}$ groups, the O atoms, S atoms and $NR_{13}$ groups are not consecutive but are separated from one another by at least one methylene group.

$C_2-C_{24}$Alkenylene is mono- or poly-unsaturated and linear or branched and is e.g. $C_2-C_{18}$- or $C_2-C_8$-alkenylene. Examples are ethenylene, propenylene, butenylene, pentenylene, hexenylene, octenylene, e.g. 1-propenylene, 1-butenylene, 3-butenylene, 2-butenylene, 1,3-pentadienylene, 5-hexenylene and 7-octenylene.

$C_2-C_{24}$Alkenylene interrupted one or more times by O, S or $NR_{13}$ is mono- or poly-unsaturated and linear or branched and is, for example, interrupted from 1 to 9 times, e.g. from 1 to 7 times or once or twice, by O, S or $NR_{13}$, and where a plurality of O, S or $NR_{13}$ is present, they are separated from one another by at least one methylene group. The meanings of $C_2-C_{24}$alkenylene are as described above.

$C_3-C_{24}$Cycloalkylene is linear or branched and may denote either a single ring or a bridged alkyl ring, for example $C_3-C_{20}$-, $C_3-C_{18}$-, $C_3-C_{12}$-, $C_4-C_{18}$-, $C_4-C_{12}$- or $C_4-C_8$-cycloalkylene, for example cyclopentylene, cyclohexylene, cyclooctylene, cyclododecylene, especially cyclopentylene and cyclohexylene, preferably cyclohexylene. $C_4-C_{18}$Cycloalkylene, however, likewise denotes structural units such as

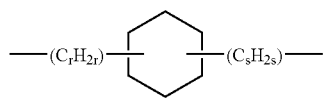

wherein r and s are each independently of the other from 0 to 12 and the sum of r+s is $\leq 12$, or

wherein r and s are each independently of the other from 0 to 13 and the sum of r+s is $\leq 13$.

$C_4-C_{18}$Cycloalkylene interrupted one or more times by O, S or $NR_{13}$ denotes a cycloalkylene unit as described above which may be interrupted both in the ring unit and in the side chain unit, for example, from 1 to 9 times, from 1 to 7 times or once or twice by O, S or $NR_{13}$.

$C_3-C_{24}$Cycloalkenylene is linear or branched and can be either a single ring or a bridged ring and is mono- or poly-unsaturated. It is, for example, $C_3-C_{12}$- or $C_3-C_8$-cycloalkenylene, for example cyclopentenylene, cyclohexenylene, cyclooctenylene, cyclododecenylene, especially cyclopentenylene or cyclohexenylene, preferably cyclohexenylene. $C_3-C_{24}$Cycloalkenylene, however, likewise denotes structural units such as

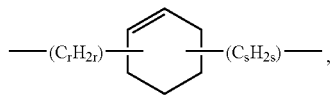

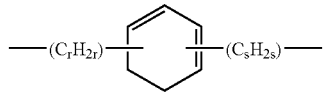

wherein r and s are each independently of the other from 0 to 12 and the sum of r+s is $\leq 12$, or

   or

wherein r and s are each independently of the other from 0 to 13 and the sum of r+s is $\leq 13$.

$C_5-C_{18}$Cycloalkenylene is as defined above for $C_3-C_{24}$cycloalkenylene up to the appropriate number of carbon atoms.

$C_3-C_{24}$Cycloalkenylene interrupted one or more times by O, S or $NR_{13}$ denotes a cycloalkenylene unit as described above which may be interrupted both in the ring unit and in the side chain unit, for example, from 1 to 9 times, from 1 to 7 times or once or twice by O, S or $NR_{13}$.

Examples are

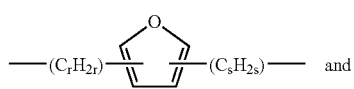   and

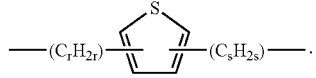

Halogen is fluorine, chlorine, bromine or iodine, especially fluorine, chlorine or bromine, preferably chlorine. $R_1$, $R_1'$, $R_2$, $R_2'$, $R_3$ and $R_3'$ as halogen are especially chlorine.

When two of the radicals $R_1$, $R_2$, $R_3$, $R_4$ and/or $R_5$ or two of the radicals $R_1'$, $R_2'$, $R_3'$, $R_4'$ and $R_5'$ are $C_1$–$C_{12}$alkylene, the following structures, for example, are formed:

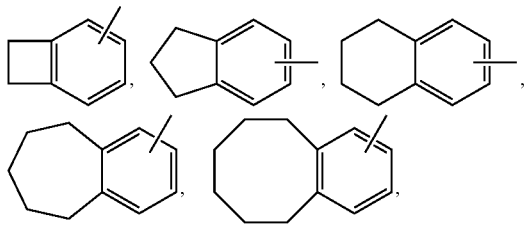

"Styryl" and "methylstyryl" are

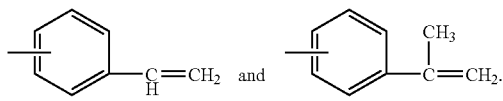

"—N═C═A" is a radical —NCO or —NCS.

Cycloalkyl substituted by —N═C═A and $C_1$–$C_4$alkyl is e.g. isophorone isocyanate.

When $R_{11}$ and $R_{12}$ together with the N atom to which they are bonded form a 5- or 6-membered ring which may also contain O or S atoms or an $NR_{13}$ group, it may be e.g. a saturated or unsaturated ring, for example aziridine, pyrrole, pyrrolidine, oxazole, thiazole, pyridine, 1,3-diazine, 1,2-diazine, piperidine or morpholine.

The term "and/or" in connection with the present Application means that not only one of the defined alternatives (substituents) may be present but several different defined alternatives (substituents) may be present together, that is to say mixtures of different alternatives (substituents) may be present.

The term "at least one" is intended to indicate "one or more than one", e.g. one or two or three, preferably one or two.

The compounds of formula I according to the invention wherein X is a radical

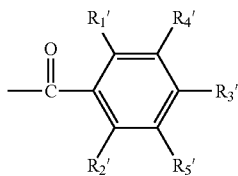

(that is to say the bisacylphosphines, oxides or sulfides) can be obtained by reaction of a dimetallated phosphine with acid halides:

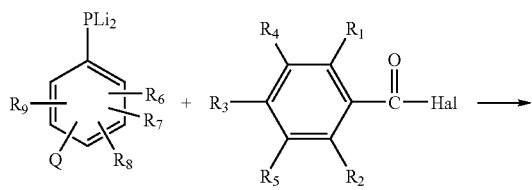

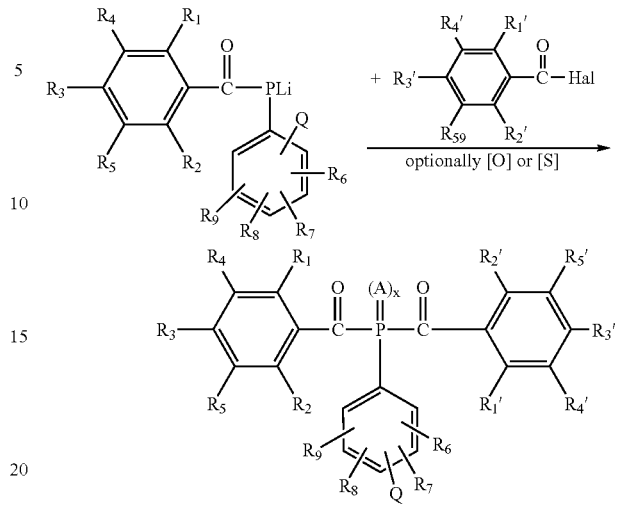

$R_1$, $R_2$, $R_3$, $R_4$, $R_5$, $R_6$, $R_7$, $R_8$, $R_9$, Q, $R_1'$, $R_2'$, $R_3'$, $R_4'$, $R_5'$, x and A are as defined above. Hal is a halogen atom, especially Cl.

For the addition of the second acid halide, it is also possible to use the same halide as that used in the first step. Thus, "symmetric" bisacylphosphine oxides of formula I can be obtained, i.e. those wherein the two acyl groups are identical.

The reaction of the starting materials is advantageously carried out in a molar ratio of 1:1, but a slight excess, for example up to 20%, of the one or the other component is not critical.

In that case too, the desired product will be formed, but the proportion of undesired secondary product can be affected.

The reaction is advantageously carried out in a solvent. It is possible to use as solvents especially ethers that are liquid at normal pressure and room temperature. Examples are dimethyl ether, diethyl ether, methyl propyl ether, 1,2-dimethoxyethane, bis(2-methoxyethyl) ether, dioxane and tetrahydrofuran. Preferably, tetrahydrofuran is used.

The reaction temperatures are advantageously from −60° C. to +120° C., e.g. from −40° C. to 100° C., for example from −20° C. to +80° C.

It is advisable to stir the reaction mixture.

It is advantageous to use the dimetallated phosphine as initial charge and to add the aryl halide dropwise thereto at the temperatures indicated above, it being possible for the aryl halide to be added as such or diluted with the reaction solvent.

If desired, the course of the reaction can be monitored by means of methods customary in the art, e.g. NMR, for example $^{31}$P-NMR, chromatography (thin-layer, HPLC, GC) etc.

In the reactions described above it is essential to work in an inert gas atmosphere, e.g. with a protective gas, such as argon or nitrogen, for the purpose of excluding atmospheric oxygen.

The reaction products can be isolated and purified by customary process steps familiar to the person skilled in the art.

Compounds of formula I wherein x=1 and A is oxygen are prepared by oxidation [O], while compounds of formula I wherein A is sulfur are prepared by thionation [S].

Prior to the oxidation or thionation, the phosphine of formula I wherein x=0 can be isolated by customary separation methods familiar to the person skilled in the art, but the reaction can also take place immediately after the foregoing reaction step without isolation of the phosphine.

For the preparation of the oxide, the oxidation of the phosphine is carried out with oxidising agents customary in the art. Suitable oxidising agents are especially hydrogen peroxide and organic peroxy compounds, for example peracetic acid or tert-butyl hydroperoxide, air or pure oxygen.

The oxidation is advantageously carried out in solution. Suitable solvents are aromatic hydrocarbons, for example benzene, toluene, m-xylene, p-xylene, ethylbenzene and mesitylene, or aliphatic hydrocarbons, e.g. alkanes and alkane mixtures, such as petroleum ether, hexane or cyclohexane. Toluene is preferably used.

During the oxidation the reaction temperature is advantageously maintained at from 0° to 120° C., preferably from 20° to 80° C.

The reaction products of formula I can be isolated and purified by customary process steps familiar to the person skilled in the art.

The preparation of the sulfide in question is carried out by reaction with sulfur, the bisacylphosphines being reacted, e.g. as such or, if desired, in a suitable inert organic solvent, with an equimolar to twice-molar amount of elemental sulfur. Suitable solvents are, for example, those described for the oxidation reactions. It is also possible, however, to use e.g. aliphatic or aromatic ethers, for example dibutyl ether, dioxane, diethylene glycol dimethyl ether or diphenyl ether, at temperatures of from 20° to 250° C., preferably from 60° to 120° C. The resulting bisacylphosphine sulfide, or the solution thereof, is advantageously freed of any elemental sulfur still present by filtration. After removal of the solvent, the bisacylphosphine sulfide can be isolated In pure form by distillation, recrystallisation or chromatographic separation methods.

It is advantageous to carry out all the above-described reactions with the exclusion of air in an inert gas atmosphere, e.g. under nitrogen or argon gas. In addition, it may be advantageous to stir the reaction mixture in question.

The compounds of formula I wherein X is a radical

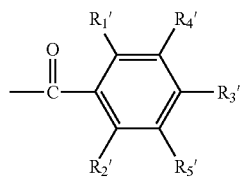

and x is 0 can be prepared, for example, also by the addition of the arylphosphines and the corresponding acid halides to an alkali-metal-containing strong base, e.g. lithium diisopropylamide or potassium hexamethyldisilazane, in an inert solvent, such as tetrahydrofuran (THF). The alkali-metal-containing strong base can also be added to a mixture of the arylphosphine with the acid halide in an inert solvent.

When $R_1$, $R_2$, $R_3$, $R_4$ and $R_5$ are identical to $R_1'$, $R_2'$, $R_3'$, $R_4'$ and $R_5'$, the addition of the acid halide is usually carried out in one step. When the above-mentioned radicals are different, the addition of the two different acid halides is advantageously carried out one after the other in two steps separated in time.

The reaction temperatures are advantageously in the range of from −78° C. to +100° C., especially from −20° C. to +50° C.

In certain cases, the preparation of the compounds of formula I wherein X is a radical

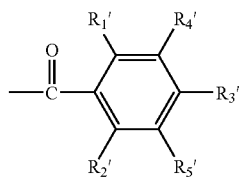

and x is 0 is carried out also by the addition of the corresponding acid halides to the arylphosphine in the presence of a tertiary base, for example triethylamine, in an inert solvent, e.g. THF or toluene.

When $R_1$, $R_2$, $R_3$, $R_4$ and $R_5$ are identical to $R_1'$, $R_2'$, $R_3'$, $R_4'$ and $R_5'$, the addition of the acid halide is carried out, for example, in one step. When the above-mentioned radicals are different, the addition of the two different acid halides can be carried out e.g. one after another in two steps separated in time.

The reaction temperatures are advantageously in the range of from −20° C. to +150° C., especially from +20° C. to +100° C.

Compounds of formula I wherein X is not an acyl radical, that is to say monoacylphosphines, oxides or sulfides, can be obtained, for example, by reaction of a dimetallated phosphine with an acyl halide and subsequent reaction with a halide (of the desired further radical):

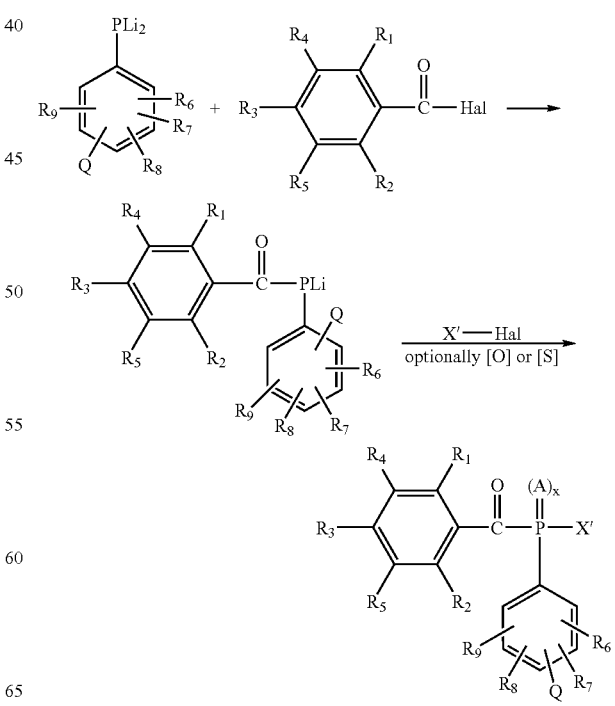

$R_1$, $R_2$, $R_3$, $R_4$, $R_5$, $R_6$, $R_7$, $R_8$, $R_9$, Q, x and A are defined as described above. X' has any of the meanings described above for X with the exception of

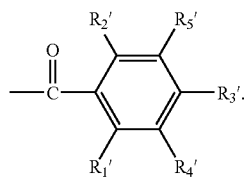

Hal is a halogen atom, especially Cl or Br.

The reaction conditions for those reactions correspond to those as described above for the bisacylphosphines, oxides and sulfides of formula I.

Monoacylphosphine compounds according to the invention wherein X is a radical $OR_{10}$ can be obtained, for example, likewise e.g. by alcoholysis of a diaminophosphine (see L. Maier, Helv. Chim. Acta 1964, 47, p. 2129 and Helv. Chim. Acta 1968, 51, p. 405) and subsequent reaction with an acyl halide in a Michaelis Arbuzov reaction:

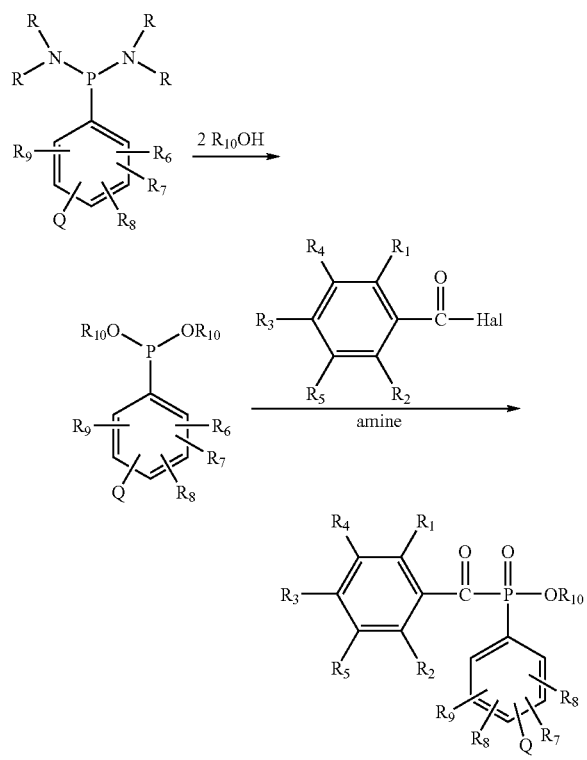

$R_1$, $R_2$, $R_3$, $R_4$, $R_5$, $R_6$, $R_7$, $R_8$, $R_9$, $R_{10}$ and Q are as defined above, Hal is a halogen, especially Cl, R is e.g. $C_1$–$C_{24}$alkyl or benzyl.

The alcoholysis of the aminophosphines is carried out by heating the aminophosphines in the corresponding alcohol at about 50° C. to 150° C. (Helv. Chim. Acta 1964, 47, p. 2129).

A further possible method of obtaining the compounds according to the invention is, for example, the Grignard reaction of an aminochlorophosphine with an arylmagnesium bromide (see H. Schmidlbauer, Monatshefte der Chemie 1965, 96, p. 1936), subsequent alcoholysis (see L. Maier, Helv. Chim. Acta 1964, 47, p. 2129 and Helv. Chim. Acta 1968, 51, p. 405) and finally reaction with an acyl halide in a Michaelis Arbuzov reaction:

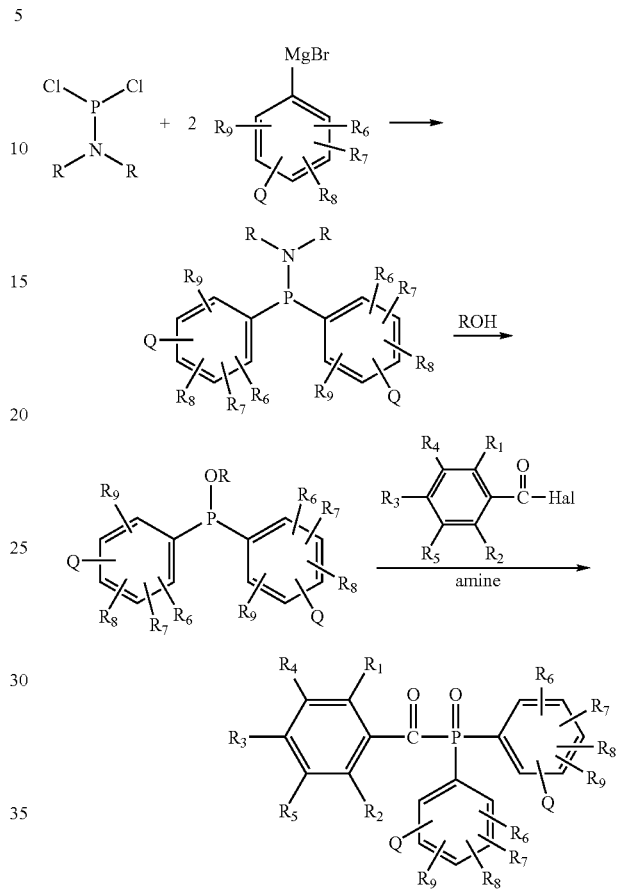

The definition of the radicals and the reaction conditions are the same as those described above.

A further possible method of obtaining monoacylphosphine compounds according to the invention is a Friedel-Crafts reaction (see Houben-Weyl, Methoden der Organischen Chemie, Vol. 12/1, p. 278ff., 295ff, 314 ff) of the Q-substituted aromatic compound with phosphorus trichloride to form the diarylchlorophosphine, followed by reduction with lithium aluminium hydride to form the diarylphosphine, subsequent reaction with butyllithium to form the metallated phosphine and finally reaction of that phosphine with the corresponding acyl halide:

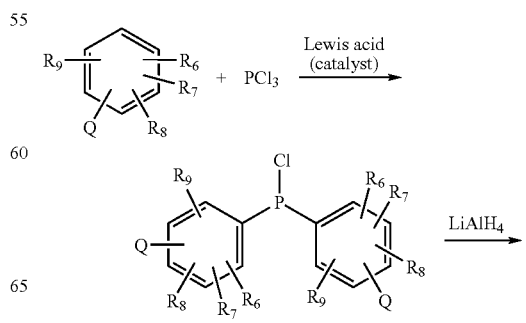

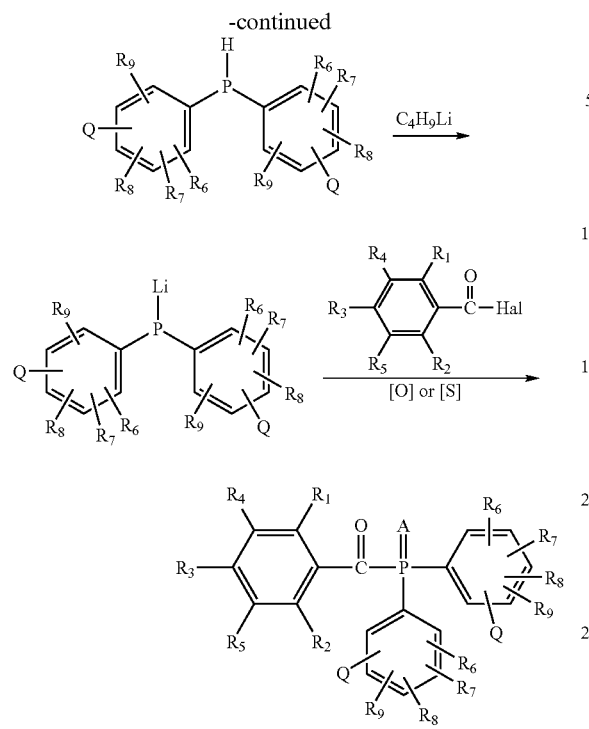

The meanings of $R_1$, $R_2$, $R_3$, $R_4$, $R_5$, $R_6$, $R_7$, $R_8$, $R_9$, Q, A and Hal are as indicated above.

Suitable Lewis acid catalysts are e.g. $AlCl_3$, $ZnCl_2$, $BiCl_3$, $TiCl_4$ and $SnCl_4$. The reaction conditions for Friedel-Crafts reactions are known to the person skilled in the art and can also be found in the literature indicated.

The Q-substituted dichloroarylphosphines required as starting materials in the above-mentioned reactions can be prepared e.g. by Friedel-Crafts reaction (see Houben-Weyl, Methoden der Organischen Chemie, Vol. 12/1, p. 278ff., 295ff, 314 ff; or, without catalyst, H. Radnitz, Chem. Ber. 1927, 60, p. 743):

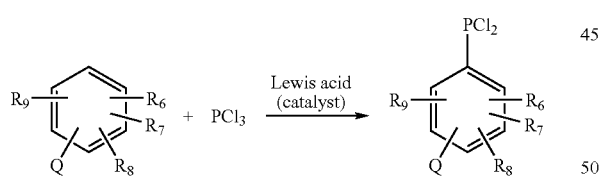

Suitable Lewis acid catalysts are e.g. $AlCl_3$, $ZnCl_2$, $BiCl_3$, $TiCl_4$ and $SnCl_4$. The meanings of the substituents are as indicated above.

The starting materials can be obtained e.g. by way of Grignard reactions (H. Schmidlbauer, Monatshefte der Chemie, 1965, 96, p. 1936):

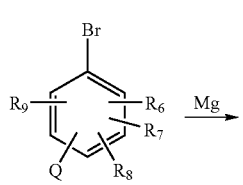

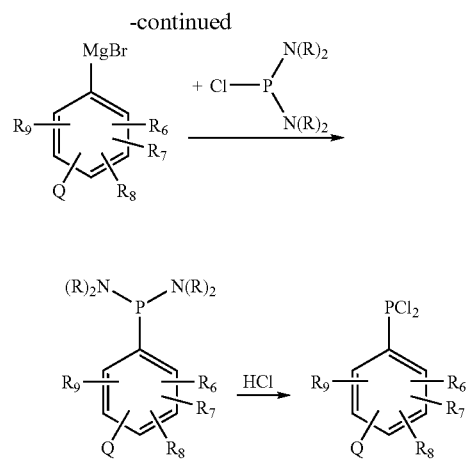

The meanings of the substituents are as indicated above.

Instead of the aryl-Grignard compound it is also possible to use the corresponding aryllithium compound (see A. H. Cowley, Inorg. Synth. 1990, 27, p. 236):

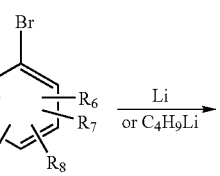

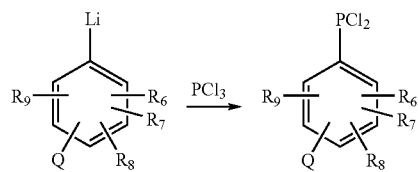

The meanings of the substituents are as indicated above.

In Helv. Chim. Acta 1964, 47, p. 2137, L. Maier describes the preparation of dichlorophosphines by means of phosphorus sulfochlorides:

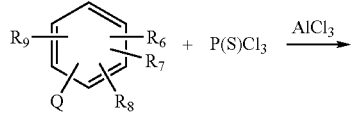

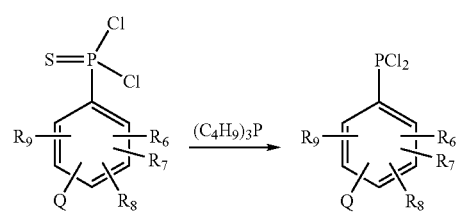

The meanings of the substituents are as indicated above.

In Zh. Obsh. Khim. 1953, 23, p. 1547, Jakubovich describes the preparation of dichlorophosphines from the corresponding silylated compounds:

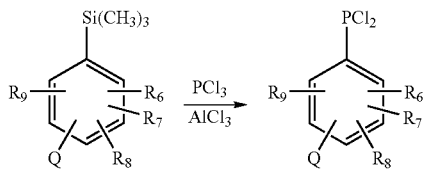

The meanings of the substituents are as described above.

Suitable arylphosphines can be prepared by reduction of the corresponding aryldichlorophosphines [Ar—P—Cl$_2$], arylphosphonic acid esters [Ar—P—O(OR')$_2$] and arylphosphonous acid esters [Ar—P(OR')$_2$] with LiAlH$_4$; SiHCl$_3$; Ph$_2$SiH$_2$ (Ph=phenyl); a) LiH, b) H$_2$O; a) Li/tetrahydrofuran, b) H$_2$O or a) Na/toluene, b) H$_2$O. Those methods are described, for example, in U.S. Pat. No. 6,020,528 (col. 5–6). Hydrogenations with LiAlH$_4$ can be found e.g. in Helv. Chim. Acta 1966, No. 96, 842.

Hydrogenation of the corresponding dichlorides (see Helv. Chim. Acta 1966, 96, p. 842):

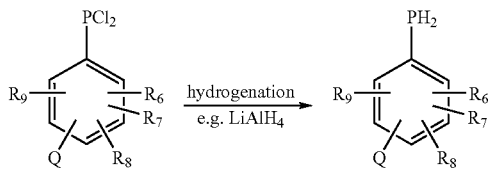

The phosphines can be obtained e.g. also from the bromides by reaction to form the phosphonic acid ester (see DE 1 810 431) and subsequent hydrogenation (see Helv. Chim. Acta 1966, 96, p. 842):

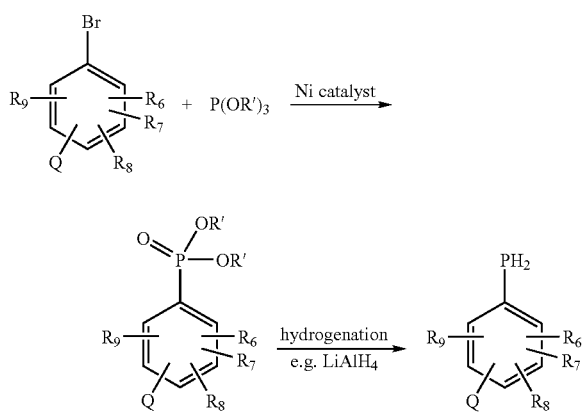

A further preparation method is, for example, reduction of the alcohol obtained by way of the corresponding phosphorus dichloride:

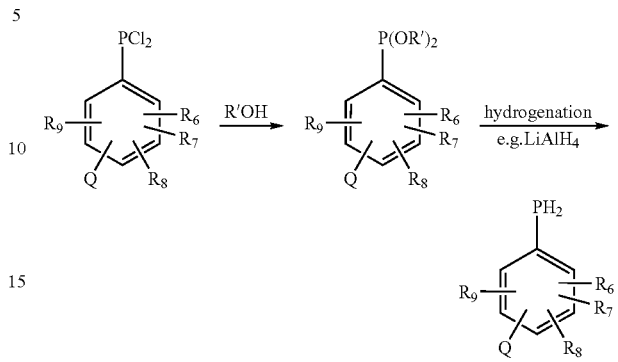

The substituents in all the above-described methods for the preparation of the starting materials correspond to those given above.

The preparation of the dimetallated arylphosphines can be carried out, for example, by reaction of suitable phosphorus halides (the preparation of which is known and is disclosed e.g. by W. Davies in J. Chem. Soc. (1935), 462 and J. Chem. Soc. (1944), 276) with the corresponding alkali metal:

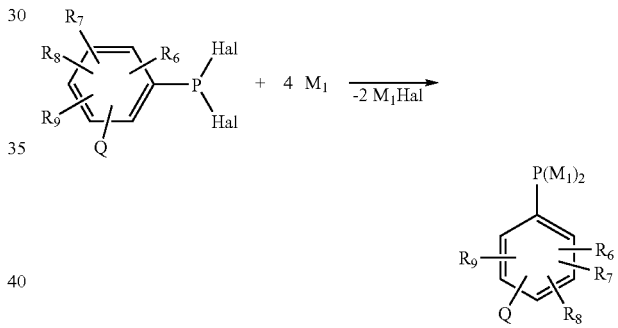

R$_6$–R$_9$, Q and Hal are as defined above.

As metal (M$_1$) there come into consideration lithium, sodium and potassium. It is also possible to use mixtures of those metals. It is advantageous to use from 4 to 8 molar equivalents of the alkali metal. The reaction is advantageously carried out in a solvent. It is possible to use as solvents especially ethers that are liquid at normal pressure and room temperature. Examples are dimethyl ether, diethyl ether, methyl propyl ether, 1,2-dimethoxyethane, bis(2-methoxyethyl)ether, dioxane and tetrahydrofuran. Preferably, tetrahydrofuran is used. The reaction temperatures are advantageously from −60° C. to +120° C. The reaction is optionally carried out with the addition of a catalyst. Catalysts that come into consideration are aromatic hydrocarbons, with or without hetero atoms, for example naphthalene, anthracene, phenanthrene, biphenyl, terphenyl, quaterphenyl, triphenylene, trans-1,2-diphenylethene, pyrene, perylene, acenaphthalene, decacyclene, quinoline, N-ethylcarbazole, dibenzothiophene and dibenzofuran.

For the preparation of the compounds of formula I according to the invention, the dimetallated compounds so obtained can be used further without isolation.

Metallated arylphosphines can be prepared, for example, also by reaction of suitable arylphosphines with the corresponding alkali metal hydride or an alkyllithium compound, optionally in the presence of a secondary amine, with the exclusion of air in an inert solvent at temperatures of e.g. from −80° C. to +120° C. It is advantageous to use from 2 to 4 molar equivalents of the alkali metal hydrides or alkyllithium compound. Suitable solvents are e.g. ethers, as described above, or inert solvents, such as alkanes, cycloalkanes, or aromatic solvents, such as toluene, xylene and mesitylene.

The acyl halides used as starting materials are known substances, some of which are commercially available, or can be prepared analogously to known compounds.

The invention relates also to compounds of formula II

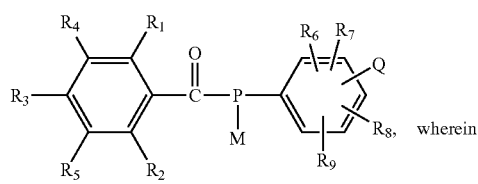

wherein
Q is $SR_{10}$ or $N(R_{11})(R_{12})$;
$R_1$, $R_2$, $R_3$, $R_4$, $R_5$, $R_6$, $R_7$, $R_8$, $R_9$ and Q are as defined above; and
M is hydrogen, Li, Na or K.

The compounds of formula II can be used as starting materials for the preparation of mono- or bis-acylphosphines, mono- or bis-acylphosphine oxides or mono- or bis-acylphosphine sulfides of formula I.

The invention accordingly relates also to a process for the preparation of compounds of formula I

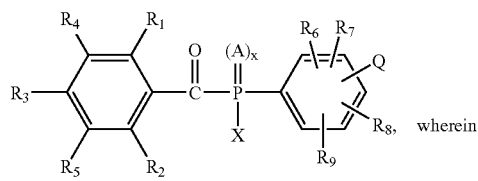

wherein
$R_1$, $R_2$, $R_3$, $R_4$, $R_5$, $R_6$, $R_7$, $R_8$, $R_9$, Q, A and x are as defined above and X is as defined above with the exception of $OR_{10}$, by reaction of a compound of formula II

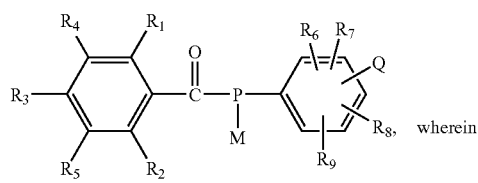

wherein
$R_1$, $R_2$, $R_3$, $R_4$, $R_5$, $R_6$, $R_7$, $R_8$, $R_9$ and Q are as defined for formula I and M is Na, Li or K, with a halide of formula (XI)

X-Hal (XI), wherein

X is as defined above and Hal is a halogen atom, especially Cl or Br, and, when compounds of formula I wherein x is 1 are to be prepared, subsequent oxidation or thionation of the resulting phosphine to form the corresponding oxide or sulfide, respectively.

The invention relates also to a process for the preparation of compounds of formula I

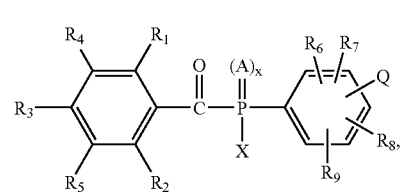

wherein
$R_1$, $R_2$, $R_3$, $R_4$, $R_5$, $R_6$, $R_7$, $R_8$, $R_9$, Q, A and x are as defined above, X is $OR_{10}$, and $R_{10}$ is as defined above, by reaction of a compound of formula X

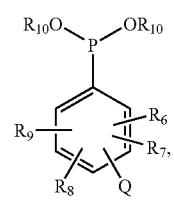

wherein
$R_6$, $R_7$, $R_8$, $R_9$, $R_{10}$ and Q are as defined for formula I, with a halide of formula (XI')

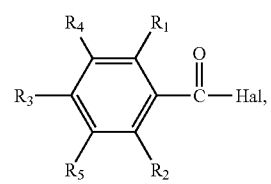

wherein
$R_1$, $R_2$, $R_3$, $R_4$ and $R_5$ are as defined above and Hal is a halogen atom, especially Cl or Br, and, when compounds of formula I wherein x is 1 are to be prepared, subsequent oxidation or thionation of the resulting phosphine to form the corresponding oxide or sulfide, respectively.

Of special interest are compounds of formulae I and II wherein $R_1$ and $R_2$ are each independently of the other $C_1$–$C_4$alkyl, $C_1$–$C_4$alkoxy, Cl or $CF_3$, especially methyl or methoxy.

$R_1$ and $R_2$ are preferably identical.

$R_1$ and $R_2$ are preferably $C_1$–$C_4$alkyl or $C_1$–$C_4$alkoxy.

$R_3$, $R_4$ and $R_5$ in the compounds of formulae I and II are especially each independently of the others hydrogen, $C_1$–$C_4$alkyl, Cl or $C_1$–$C_4$alkoxy, more especially hydrogen, methyl or methoxy.

Preferably $R_3$ is $C_1$–$C_4$alkyl, or $C_1$–$C_4$alkoxy, especially methyl, methoxy or hydrogen and $R_4$ and $R_5$ are hydrogen.

The preferred meanings of $R_1'$, $R_2'$, $R_3'$, $R_4'$ and $R_5'$ apply analogously to those described for $R_1$, $R_2$, $R_3$, $R_4$ and $R_5$.

$R_6$, $R_7$, $R_8$ and $R_9$ in the compounds of formulae I and II are especially each independently of the others hydrogen, $C_1$–$C_{12}$alkyl; $OR_{10}$, phenyl or halogen, preferably $C_1$–$C_4$alkyl, $C_1$–$C_4$-alkoxy, phenyl or halogen. $R_6$, $R_7$, $R_8$, $R_9$ and $R_{10}$ in the compounds of formulae I and II are preferably hydrogen, $C_1$–$C_4$alkyl or $C_1$–$C_4$alkoxy, especially hydrogen.

$R_{10}$, $R_{11}$ and $R_{12}$ in the compounds of formulae I and II are, for example, hydrogen, $C_1$–$C_{12}$-alkyl, cyclopentyl, cyclohexyl, phenyl, benzyl, or $C_2$–$C_{12}$alkyl which is interrupted one or more times by O, preferably $C_1$–$C_4$alkyl, cyclopentyl, cyclohexyl, phenyl or benzyl.

Also of interest are compounds wherein $R_{11}$ and $R_{12}$ are e.g. hydrogen, $C_1$–$C_4$alkyl, phenyl or benzyl, or $C_2$–$C_{12}$alkyl which is interrupted one or more times by non-consecutive O atoms and which is unsubstituted or substituted by OH and/or SH; or $R_{11}$ and $R_{12}$ together with the N atom to which they are bonded are piperidino, morpholino, pyrrolo or piperazino. Preferably $R_{11}$ and $R_{12}$ are $C_1$–$C_4$alkyl, or $R_{11}$ and $R_{12}$ together are morpholino or pyrrolo.

$R_{13}$ in the compounds of formulae I and II is especially hydrogen, phenyl, $C_1$–$C_4$alkyl, or $C_2$–$C_4$alkyl which is interrupted one or more times by O or S and which is unsubstituted or substituted by OH and/or SH, preferably hydrogen or $C_1$–$C_4$alkyl.

M in the compounds of formula II is preferably hydrogen or Li, especially Li.

A is preferably O.

Of special interest are compounds of formulae I and II wherein $R_1$ and $R_2$ are each independently of the other $C_1$–$C_{12}$alkyl, $OR_{10}$, $CF_3$ or halogen;

$R_3$, $R_4$ and $R_5$ are each independently of the others hydrogen, $C_1$–$C_{12}$alkyl, $OR_{10}$ or halogen;

$R_6$, $R_7$, $R_8$ and $R_9$ are each independently of the others hydrogen, $C_1$–$C_{12}$alkyl, $OR_{10}$, phenyl or halogen;

$R_{10}$ is hydrogen, $C_1$–$C_{12}$alkyl, cyclohexyl, cyclopentyl, phenyl or benzyl;

$R_{13}$ is hydrogen or $C_1$–$C_{12}$alkyl; and in the compounds of formula I
A is O; and
x is 1; and in the compounds of formula II
M is hydrogen or Li.

Also of special interest are compounds of formulae I and II wherein $R_1$, $R_2$, $R_3$, $R_1'$, $R_2'$ and $R_3'$ are methyl, X is a radical

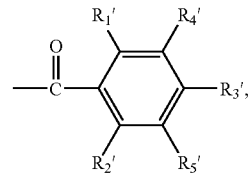

x is 1 and A is O and $R_6$, $R_7$, $R_8$ and $R_9$ are hydrogen.

Also of interest are compounds of formulae I and II wherein $R_1$, $R_2$ and $R_3$ are methyl, x is 1 and A is O, $R_6$, $R_7$, $R_8$ and $R_9$ are hydrogen and X is $OR_{10}$ or a radical

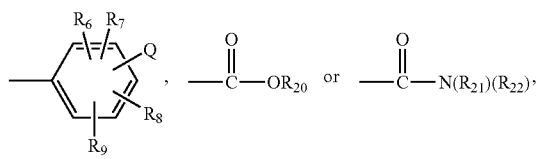

the radicals $R_{20}$, $R_{21}$ and $R_{22}$ being as defined above.

Especially of interest are those compounds of formulae I and II wherein $R_{10}$, $R_{11}$ and $R_{12}$ are each independently of the others $C_1$–$C_{24}$alkyl, or $C_2$–$C_{20}$alkyl which is interrupted one or more times by non-consecutive O atoms; or $R_{11}$ and $R_{12}$ together with the N atom to which they are bonded form a 5- or 6-membered ring, which may also contain O atoms. $R_{10}$, $R_{11}$ and $R_{12}$ are preferably $C_1$–$C_{24}$alkyl.

Preference is given to compounds of formula I wherein
A is O;
x is 1;
Q is $SR_{10}$ or $N(R_{11})(R_{12})$;
$R_1$ and $R_2$ are each independently of the other $C_1$–$C_{12}$alkyl, $OR_{10}$, $CF_3$ or halogen;
$R_3$, $R_4$ and $R_5$ are each independently of the others hydrogen, $C_1$–$C_{12}$alkyl, $OR_{10}$ or halogen;
$R_6$, $R_7$, $R_8$ and $R_9$ are each independently of the others hydrogen, $C_1$–$C_{12}$alkyl, $OR_{10}$, halogen, or phenyl unsubstituted or substituted one or more times by $C_1$–$C_4$alkyl;
$R_{10}$, $R_{11}$ and $R_{12}$ are each independently of the others hydrogen, $C_1$–$C_{12}$alkyl, $C_3$–$C_8$cycloalkyl, $C_2$–$C_{12}$alkenyl, phenyl, benzyl, or $C_2$–$C_{20}$alkyl which is interrupted one or more times by non-consecutive O atoms and which is unsubstituted or substituted by OH and/or SH; or
$R_{11}$ and $R_{12}$ together with the N atom to which they are bonded form a 5- or 6-membered ring, which may also contain O atoms or a $NR_{13}$ group;
$R_{13}$ is hydrogen or $C_1$–$C_{12}$alkyl;

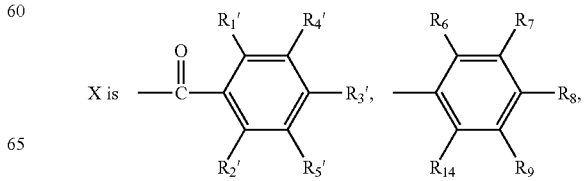

-continued

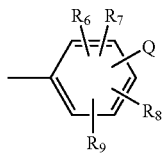

or OR$_{10}$ or X is C$_1$–C$_{24}$alkyl which is unsubstituted or substituted one or more times by OR$_{15}$, SR$_{15}$, N(R$_{16}$)(R$_{17}$), phenyl, halogen, CN,

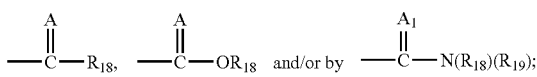

or X is C$_2$–C$_{24}$alkyl which is interrupted one or more times by O, S or NR$_{13}$ and which is unsubstituted or substituted by OR$_{15}$, SR$_{15}$, N(R$_{16}$)(R$_{17}$), phenyl, halogen,

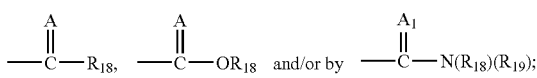

or X is C$_1$–C$_{24}$alkoxy which is uninterrupted or interrupted one or more times by O, S or NR$_{13}$ and which is unsubstituted or substituted one or more times by OR$_{15}$, SR$_{15}$, N(R$_{16}$)(R$_{17}$), phenyl, CN,

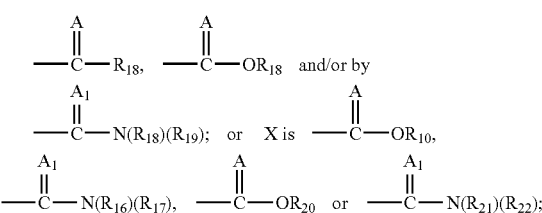

or X is C$_2$–C$_{24}$alkenyl unsubstituted or substituted by C$_6$–C$_{14}$aryl, CN, (CO)OR$_{15}$ or by (CO)N(R$_{18}$)(R$_{19}$);

R$_1'$ and R$_2'$ each independently of the other has one of the meanings given for R$_1$ and R$_2$; and R$_3'$, R$_4'$ and R$_5'$ each independently of the others has one of the meanings given for R$_3$, R$_4$ and R$_5$;

R$_{14}$ has one of the meanings given for R$_6$, R$_7$, R$_8$ and R$_9$;

R$_{15}$, R$_{16}$ and R$_{17}$ each independently of the others has one of the meanings given for R$_{10}$;

R$_{18}$ and R$_{19}$ are each independently of the other hydrogen, C$_1$–C$_{24}$alkyl, C$_2$–C$_{12}$alkenyl, C$_3$–C$_8$cycloalkyl, phenyl, benzyl; or C$_2$–C$_{20}$alkyl which is interrupted one or more times by O or S;

R$_{20}$ is C$_1$–C$_{20}$alkyl which is substituted one or more times by OR$_{15}$ or halogen; or C$_2$–C$_{20}$alkyl which is interrupted one or more times by non-consecutive O atoms and which is unsubstituted or substituted one or more times by OR$_{15}$ or halogen; or R$_{20}$ is C$_2$–C$_{20}$alkenyl; and R$_{21}$ and R$_{22}$ are each independently of the other hydrogen; C$_1$–C$_{20}$alkyl which is substituted one or more times by OR$_{15}$, halogen, styryl, methylstyryl or by —N=C=A; or C$_2$–C$_{20}$alkyl which is interrupted one or more times by non-consecutive O atoms and which is unsubstituted or substituted one or more times by OR$_{15}$, halogen, styryl or by methylstyryl.

Also preferred are compounds of formula I or II wherein

A is O;

x is 0 or 1;

Q is SR$_{10}$ or N(R$_{11}$)(R$_{12}$);

R$_1$ and R$_2$ are each independently of the other C$_1$–C$_4$alkyl;

R$_3$, R$_4$ and R$_5$ are each independently of the others hydrogen or C$_1$–C$_4$alkyl;

R$_6$, R$_7$, R$_8$ and R$_9$ are hydrogen;

R$_{10}$, R$_{11}$ and R$_{12}$ are each independently of the others C$_1$–C$_4$alkyl, C$_2$–C$_4$alkenyl, or C$_2$–C$_4$alkyl which is interrupted by non-consecutive O atoms; or R$_{11}$ and R$_{12}$ together with the N atom to which they are bonded form a 5- or 6-membered ring, which may also contain O atoms;

in the compounds of formula I

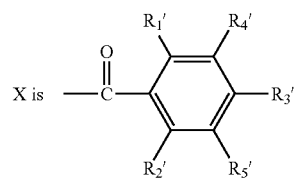

or OR$_{10}$ or X is C$_1$–C$_{12}$alkyl which is unsubstituted or substituted one or more times by OR$_{15}$, phenyl,

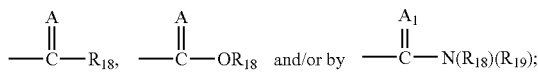

or X is C$_2$–C$_{12}$alkyl which is interrupted one or more times by O and which is unsubstituted or substituted by OR$_{15}$, phenyl,

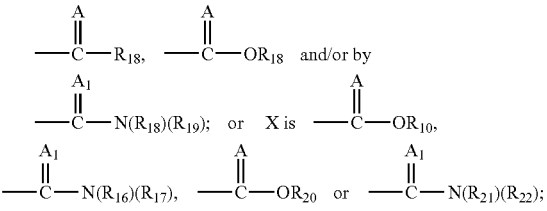

or X is C$_2$–C$_{12}$alkenyl unsubstituted or substituted by C$_6$–C$_{10}$aryl, CN or by (CO)OR$_{15}$;

R$_1'$ and R$_2'$ each independently of the other has one of the meanings given for R$_1$ and R$_2$;

R$_3'$, R$_4'$ and R$_5'$ each independently of the others has one of the meanings given for R$_3$, R$_4$ and R$_5$;

R$_{15}$, R$_{16}$ and R$_{17}$ each independently of the others has one of the meanings given for R$_{10}$;

R$_{18}$ and R$_{19}$ are each independently of the other hydrogen, C$_1$–C$_4$alkyl, phenyl, benzyl; or C$_2$–C$_6$alkyl which is interrupted one or more times by O;

R$_{20}$ is C$_1$–C$_6$alkyl which is substituted one or more times by OR$_{15}$; or C$_2$–C$_6$alkyl which is interrupted one or more times by non-consecutive O atoms and which is unsubstituted or substituted one or more times by OR$_{15}$; or R$_{20}$ is C$_2$–C$_4$alkenyl; and $R_{21}$ and $R_{22}$ are each independently of the other hydrogen or $C_1$–$C_{20}$alkyl; and in the compounds of formula II M is Li.

Special preference is given to compounds of formulae I and II wherein

A is O;

x is 0 or 1;

Q is $SR_{10}$ or $N(R_{11})(R_{12})$;

$R_1$ and $R_2$ are each independently of the other $C_1$–$C_4$alkyl;

$R_3$, $R_4$ and $R_5$ are each independently of the others hydrogen or $C_1$–$C_4$alkyl;

$R_6$, $R_7$, $R_8$ and $R_9$ are hydrogen;

$R_{10}$, $R_{11}$ and $R_{12}$ are each independently of the others $C_1$–$C_4$alkyl, or $C_2$–$C_4$alkyl which is interrupted by non-consecutive O atoms; or $R_{11}$ and $R_{12}$ together with the N atom to which they are bonded form a 5- or 6-membered ring, which may also contain O atoms;

in the compounds of formula I

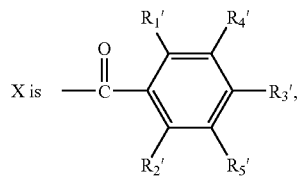

or $C_1$–$C_4$alkyl which is substituted by phenyl;

$R_1'$ and $R_2'$ each independently of the other has one of the meanings given for $R_1$ and $R_2$;

$R_3'$, $R_4'$ and $R_5'$ each independently of the others has one of the meanings given for $R_3$, $R_4$ and $R_5$; and in the compounds of formula II M is Li.

The compounds of formula I are photoinitiators and can be used for photopolymerisation of compounds that contain ethylenically unsaturated bonds. The invention therefore relates also to photopolymerisable compositions comprising (a) at least one ethylenically unsaturated photopolymerisable compound and (b) as photoinitiator at least one compound of formula I, it being possible for the composition also to comprise, in addition to component (b), other photoinitiators (c) and/or other additives (d).

It is preferable to use in those compositions compounds of formula I wherein x is 1, especially those compounds wherein x is 1 and A is oxygen.

The unsaturated compounds may contain one or more olefinic double bonds. They may be low molecular weight (monomeric) or higher molecular weight (oligomeric). Examples of monomers having a double bond are alkyl and hydroxyalkyl acrylates and methacrylates, e.g. methyl, ethyl, butyl, 2-ethylhexyl and 2-hydroxyethyl acrylate, isobornyl acrylate and methyl and ethyl methacrylate. Also of interest are resins modified with silicon or fluorine, e.g. silicone acrylates. Further examples are acrylonitrile, acrylamide, methacrylamide, N-substituted (meth)acrylamides, vinyl esters, such as vinyl acetate, vinyl ethers, such as iso-butyl vinyl ether, styrene, alkyl- and halo-styrenes, N-vinylpyrrolidone, vinyl chloride and vinylidene chloride.

Examples of monomers having a plurality of double bonds are ethylene glycol diacrylate, propylene glycol diacrylate, neopentyl glycol diacrylate, hexamethylene glycol diacrylate and bisphenol-A diacrylate, 4,4'-bis(2-acryloyloxyethoxy)diphenylpropane, trimethylolpropane triacrylate, pentaerythritol triacrylate and pentaerythritol tetraacrylate, vinyl acrylate, divinylbenzene, divinyl succinate, diallyl phthalate, triallyl phosphate, triallyl isocyanurate and tris(2-acryloylethyl)isocyanurate.

Examples of higher molecular weight (oligomeric) polyunsaturated compounds are acrylated epoxy resins, acrylated or vinyl-ether- or epoxy-group-containing polyesters, polyurethanes and polyethers. Further examples of unsaturated oligomers are unsaturated polyester resins, which are usually produced from maleic acid, phthalic acid and one or more diols and have molecular weights of about from 500 to 3000. In addition it is also possible to use vinyl ether monomers and oligomers, and also maleate-terminated oligomers having polyester, polyurethane, polyether, polyvinyl ether and epoxide main chains. Combinations of vinylether-group-carrying oligomers and polymers, as described in WO 90/01512, are especially suitable, but copolymers of monomers functionalised with maleic acid and vinyl ether also come into consideration. Such unsaturated oligomers can also be termed prepolymers.

Especially suitable are, for example, esters of ethylenically unsaturated carboxylic acids and polyols or polyepoxides, and polymers having ethylenically unsaturated groups in the chain or in side groups, e.g. unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more such polymers.

Examples of unsaturated carboxylic acids are acrylic acid, methacrylic acid, crotonic acid, itaconic acid, cinnamic acid and unsaturated fatty acids such as linolenic acid and oleic acid. Acrylic and methacrylic acid are preferred.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)propane, and novolaks and resoles. Examples of polyepoxides are those based on the said polyols, especially the aromatic polyols and epichlorohydrin. Also suitable as polyols are polymers and copolymers that contain hydroxyl groups in the polymer chain or in side groups, e.g. polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols include alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxy-ethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Examples of esters are:

trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

Also suitable as component (a) are the amides of identical or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-(β-aminoethyl ether, diethylenetriamine, triethylenetetramine and di(β-aminoethoxy)- and di(β-aminopropoxy)ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, diethylenetriamine trismethacrylamide, bis(methacrylamidopropoxy)ethane, finethacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They may be used together with ethylenically unsaturated comonomers, e.g. styrene. The polyesters and polyamides may also be derived from dicarboxylic acids and ethylenically unsaturated diols or diamines, especially from those having longer chains of e.g. from 6 to 20 carbon atoms. Examples of polyurethanes are those composed of saturated diisocyanates and unsaturated diols or unsaturated diisocyanates and saturated diols.

Polybutadiene and polyisoprene and copolymers thereof are known. Suitable comonomers include, for example, olefins, such as ethylene, propene, butene and hexene, (meth)acrylates, acrylonitrile, styrene and vinyl chloride. Polymers having (meth)acrylate groups in the side chain are likewise known. Examples are reaction products of novolak-based epoxy resins with (meth)acrylic acid; homo- or co-polymers of vinyl alcohol or hydroxyalkyl derivatives thereof that have been esterified with (meth)acrylic acid; and homo- and co-polymers of (meth)acrylates that have been esterified with hydroxyalkyl(meth)acrylates.

The photopolymerisable compounds can be used on their own or in any desired mixtures. Preferably mixtures of polyol (meth)acrylates are used.

Binders may also be added to the compositions according to the invention, this being particularly advantageous when the photopolymerisable compounds are liquid or viscous substances. The amount of binder may be, for example, from 5 to 95% by weight, preferably from 10 to 90% by weight and especially from 40 to 90% by weight, based on total solids. The choice of binder is made in accordance with the field of use and the properties required therefor, such as developability in aqueous and organic solvent systems, adhesion to substrates and sensitivity to oxygen.

Suitable binders are, for example, polymers having a molecular weight of approximately from 5000 to 2 000 000, preferably from 10 000 to 1 000 000. Examples are: homo- and copolymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, such as cellulose acetate, cellulose acetate butyrate, methylcellulose, ethylcellulose; polyvinylbutyral, polyvinylformal, cyclised caoutchouc, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide), polyesters such as poly(ethylene glycol terephthalate) and poly(hexamethylene glycol succinate).

The unsaturated compounds can also be used in admixture with non-photopolymerisable film-forming components. These may be, for example, physically drying polymers or solutions thereof in organic solvents, for example nitrocellulose or cellulose acetobutyrate, but they may also be chemically or thermally curable resins, for example polyisocyanates, polyepoxides or melamine resins. The concomitant use of thermally curable resins is important for use in so-called hybrid systems, which are photopolymerised in a first step and crosslinked by thermal after-treatment in a second step.

The photoinitiators according to the invention are also suitable as initiators for the curing of oxidatively drying systems, as described e.g. in "Lehrbuch der Lacke und Beschichtungen" Vol III, 296–328, Verlag W. A. Colomb in der Heenemann GmbH, Berlin-Oberschwandorf (1976).

The photopolymerisable mixtures may also comprise various additives (d) in addition to the photoinitiator. Examples thereof are thermal inhibitors, which are intended to prevent premature polymerisation, e.g. hydroquinone, hydroquinone derivatives, p-methoxyphenol, β-naphthol or sterically hindered phenols, e.g. 2,6-di(tert-butyl)-p-cresol. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N,N-diethylhydroxylamine. For the purpose of excluding atmospheric oxygen during polymerisation it is possible to add paraffin or similar wax-like substances which, being insoluble in the polymer, migrate to the surface at the beginning of the polymerisation and form a transparent surface layer which prevents air from entering. Equally possible is the application of a layer that is impermeable to oxygen. As light stabilisers it is possible to add UV absorbers, e.g. those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS).

The following are examples of such UV absorbers and light stabilisers:

1. 2-(2'-Hydroxyphenyl)-benzotriazoles, e.g. 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)-phenyl)-benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3', 5'-di-tert-amyl-2'-hydroxyphenyl)-benzotriazole, 2-(3',5'-bis(α,α-dimethylbenzyl)-2'-hydroxyphenyl)benzotriazole, a mixture of 2-(3'-tert-butyl-2'-hydroxy-5'-(2-octyloxycarbonylethyl)-phenyl)-5-chlorobenzotriazole, 2-(3'-tert-butyl-5'-[2-(2-ethylhexyloxy)-carbonylethyl]-2'-hydroxyphenyl)-5-chlorobenzotriazole, 2-(3'-tert-butyl-2'-hydroxy-5'-(2-methoxycarbonylethyl)-phenyl)-5-chlorobenzotriazole, 2-(3'-tert-butyl-2'-hydroxy-5'-(2-methoxycarbonylethyl)-phenyl)-benzotriazole, 2-(3'-tert-butyl-2'-hydroxy-5'-(2-octyloxycarbonylethyl)-phenyl)-benzotriazole, 2-(3'-tert-butyl-5'-[2-(2-ethylhexyloxy)-carbonylethyl]-2'-hydroxyphenyl)-benzotriazole, 2-(3'-dodecyl-2'-hydroxy-5'-methylphenyl)-benzotriazole and 2-(3'-tert-butyl-2'-hydroxy-5'-(2-isooctyloxycarbonylethyl)-phenyl-benzotriazole, 2,2'-methylene-bis[4-(1,1,3,3-tetramethylbutyl)-6-benzotriazol-2-yl-phenol]; the transesterification product of 2-[3'-tert-butyl-5'-(2-methoxycarbonylethyl)-2'-hydroxyphenyl]-benzotriazole with polyethylene glycol 300; [R—CH$_2$CH$_2$—COO(CH$_2$)$_3$]$_2$— wherein R=3'-tert-butyl-4'-hydroxy-5'-2H-benzotriazol-2-yl-phenyl.

2. 2-Hydroxybenzophenones, e.g. a 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.

3. Esters of unsubstituted or substituted benzoic acids, e.g. 4-tert-butyl-phenyl salicylate, phenyl salicylate, octylphenyl salicylate, dibenzoylresorcinol, bis(4-tert-butylbenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butylhydroxybenzoic acid octadecyl ester and 3,5-di-tert-butylhydroxybenzoic acid 2-methyl-4,6-di-tert-butylphenyl ester.

4. Acrylates, e.g. α-cyano-β,β-diphenylacrylic acid ethyl ester or isooctyl ester, α-methoxycarbonylcinnamic acid methyl ester, α-cyano-β-methyl-p-methoxycinnamic acid methyl ester or butyl ester, α-methoxycarbonyl-p-methoxycinnamic acid methyl ester and N-(β-methoxycarbonyl-β-cyanovinyl)-2-methyl-indoline.

5. Sterically hindered amines, e.g. bis(2,2,6,6-tetramethylpiperidyl) sebacate, bis(2,2,6,6-tetramethyl-piperidyl) succinate, bis(1,2,2,6,6-pentamethylpiperidyl) sebacate, n-butyl-3,5-ditert-butyl-4-hydroxybenzyl-malonic acid bis (1,2,2,6,6-pentamethylpiperidyl)ester, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the condensation product of N,N'-bis(2,2,6,6-tetramethyl-4-piperidyl)hexamethylenediamine and 4-morpholino-2,6-dichloro-1,3,5-triazine, the condensation product of 2-chloro-4,6-di(4-n-butylamino-2,2,6,6-tetramethylpiperidyl)-1,3,5-triazine and 1,2-bis(3-aminopropylamino)ethane, the condensation product of 2-chloro-4,6-di(4-n-butylamino-1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro[4.5]-decane-2,4-dione, 3-dodecyl-1-(2,2,6,6-tetramethyl-4-piperidyl)-pyrrolidine-2,5-dione, 3-dodecyl-1-(1,2,2,6,6-pentamethyl-4-piperidyl)-pyrrolidine-2,5-dione, 2,4-bis[N-(1-cyclohexyloxy-2,2,6-6-tetramethylpiperidin-4-yl)-n-butyl-amino]-6-(2-hydroxyethyl)amino-1,3,5-triazine, the condensation product of 2,4-bis[1-cyclohexyloxy-2,2,6,6-tetramethylpiperidin-4-yl)butylamino]-6-chloro-s-triazine and N,N'-bis(3-aminopropyl)ethylenediamine.

6. Oxalic acid diamides, e.g. 4,4'-dioctyloxy-oxanilide, 2,2'-diethoxy-oxanilide, 2,2'-dioctyloxy-5,5'-di-tert-butyl oxanilide, 2,2'-didodecyloxy-5,5'-di-tert-butyl oxanilide, 2-ethoxy-2'-ethyl oxanilide, N,N'-bis(3-dimethylaminopropyl)oxalamide, 2-ethoxy-5-tert-butyl-2'-ethyl oxanilide and a mixture thereof with 2-ethoxy-2'-ethyl-5,4'-di-tert-butyl oxanilide and mixtures of o- and p-methoxy- and of o- and p-ethoxy-disubstituted oxanilides. 7. 2-(2-Hydroxyphenyl)-1,3,5-triazines, e.g. 2,4,6-tris(2-hydroxy-4-octyloxyphenyl)-1,3,5-triazine, 2-(2-hydroxyoctyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy4-(2-hydroxy-3-butyloxy-propyloxy)-phenyl]-4,6-bis(2,4-dimethylphenyl)-1,3,5-triazine, 2-[2-hydroxy-4-(2-hydroxy-3-octyloxy-propyloxy)-phenyl]-4,6-bis(2,4-dimethylphenyl)-1,3,5-triazine and 2-[4-dodecyloxy/tridecyloxy-(2-hydroxypropyl)oxy-2-hydroxyphenyl]4,6-bis(2,4-dimethylphenyl)-1,3,5-triazine.

8. Phosphites and phosphonites, e.g. triphenyl phosphite, diphenylalkyl phosphites, phenyldialkyl phosphites, tris (nonylphenyl) phosphite, trilauryl phosphite, trioctadecyl phosphite, distearyl-pentaerythritol diphosphite, tris(2,4-di-tert-butylphenyl) phosphite, diisodecylpentaerythritol diphosphite, bis(2,4-di-tert-butylphenyl)pentaerythritol diphosphite, bis(2,6-di-tert-butyl-4-methylphenyl)pentaerythritol diphosphite, bis-isodecyloxy-pentaerythritol diphosphite, bis(2,4-di-tert-butyl-6-methylphenyl)pentaerythritol diphosphite, bis(2,4,6-tri-tert-butylphenyl)pentaerythritol diphosphite, tristearyl sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl)methyl phosphite and bis(2,4-di-tert-butyl-6-methylphenyl)ethyl phosphite.

Examples of UV absorbers and light stabilisers suitable as components (d) include "Krypto-UVA" as described e.g. in EP 180 548. It is also possible to use latent UV absorbers, as described e.g. by Hida et al in RadTech Asia 97, 1997, page 212.

Additives customary in the art, e.g. antistatics, flow improvers and adhesion enhancers, can also be used.

In order to accelerate the photopolymerisation it is possible to add as further additives (d) a large number of amines, e.g. triethanolamine, N-methyl-diethanolamine, p-dimethylamino-benzoic acid ethyl ester or Michler's ketone. The action of the amines can be enhanced by the addition of aromatic ketones e.g. of the benzophenone type. Amines suitable for use as oxygen capture agents are, for example, substituted N,N-dialkylanilines, as described in EP 339 841. Further accelerators, co-initiators and auto-oxidisers are thiols, thioethers, disulfides and phosphines, as described e.g. in EP 438 123 and GB 2 180 358.

It is also possible for chain-transfer reagents customary in the art to be added to the compositions according to the invention. Examples are mercaptans, amines and benzothiazole.

Photopolymerisation can also be accelerated by the addition, as further additives (d), of photosensitisers that shift or broaden the spectral sensitivity. These include especially aromatic carbonyl compounds, e.g. benzophenone, thioxanthone, including especially isopropylthioxanthone, anthraquinone and 3-acylcoumarin derivatives, terphenyls, styryl ketones, and 3-(aroylmethylene)-thiazolines, camphorquinone and also eosin, rhodamine and erythrosine dyes.

The amines mentioned above, for example, can also be considered as photosensitisers.

Further examples of such photosensitisers are

1. Thioxanthones

Thioxanthone, 2-isopropylthioxanthone, 2-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di[2-(2-methoxyethoxy)ethoxycarbonyl]thioxanthone, 1-ethoxycarbonyl-3-(1-methyl-1-morpholinoethyl)thioxanthone, 2-methyl-6-dimethoxymethyl-thioxanthone, 2-methyl-6-(1,1-dimethoxybenzyl)thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-polyethylene glycol ester, 2-hydroxy-3-(3,4-dimethyl-9-oxo-9H-thioxanthon-2-yloxy)-N,N,N-trimethyl-1-propanaminium chloride;

2. Benzophenones

Benzophenone, 4-phenylbenzophenone, 4-methoxybenzophenone, 4,4'-dimethoxybenzophenone, 4,4'-dimethylbenzophenone, 4,4'-dichlorobenzophenone, 4,4'-dimethylaminobenzophenone, 4,4'-diethylaminobenzophenone, 4-methylbenzophenone, 2,4,6-trimethylbenzophenone, 4-(4-methylthiophenyl)-benzophenone, 3,3'-dimethyl-4-methoxybenzophenone, methyl 2-benzoylbenzoate, 4-(2-hydroxyethylthio)-benzophenone, 4-(4-tolylthio)benzophenone, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl)-benzophenone, 4-benzoyl-N,N-dimethyl-N-[2-(1-oxo-2-propenyl)oxy]ethyl-benzenemethanaminium chloride;

3. 3-Acylcoumarins

3-Benzoylcoumarin, 3-benzoyl-7-methoxycoumarin, 3-benzoyl-5,7-di(propoxy)coumarin, 3-benzoyl-6,8-dichlorocoumarin, 3-benzoyl-6-chlorocoumarin, 3,3'-carbonyl-bis[5,7-di(propoxy)coumarin], 3,3'-carbonyl-bis(7-methoxycoumarin), 3,3'-carbonyl-bis(7-diethylaminocoumarin), 3-isobutyroylcoumarin, 3-benzoyl-5,7-dimethoxycoumarin, 3-benzoyl-5,7-diethoxycoumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-dimethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin;

4. 3-(Aroylmethylene)-thiazolines

3-Methyl-2-benzoylmethylene-β-naphthothiazoline, 3-methyl-2-benzoylmethylene-benzothiazoline, 3-ethyl-2-propionylmethylene-β-naphthothiazoline;

5. Other Carbonyl Compounds

Acetophenone, 3-methoxyacetophenone, 4-phenylacetophenone, benzil, 2-acetylnaphthalene, 2-naphthaldehyde, 9,10-anthraquinone, 9-fluorenone, dibenzosuberone, xanthone, 2,5-bis(4-diethylaminobenzylidene)cyclopentanone, α-(para-dimethylaminobenzylidene)ketones, such as 2-(4-dimethylamino-benzylidene)-indan-1-one or 3-(4-dimethylaminophenyl)-1-indan-5-yl-propenone, 3-phenylthiophthalimide, N-methyl-3,5-di(ethylthio)phthalimide.

The curing process, especially in the case of pigmented compositions (e.g. compositions pigmented with titanium dioxide), may also be assisted by the addition, as additional additive (d), of a component that forms free radicals under thermal conditions, e.g. an azo compound, such as 2,2'-azobis(4-methoxy-2,4-dimethylvaleronitrile), a triazene, diazosulfide, pentazadiene or a peroxy compound, for example a hydroperoxide or peroxycarbonate, e.g. tert-butyl hydroperoxide, as described e.g. in EP 245 639.

The compositions according to the invention may also comprise as further additives (d) a photoreducible dye, e.g. a xanthene, benzoxanthene, benzothioxanthene, thiazine, pyronin, porphyrin or acridine dye, and/or a radiation-cleavable trihalomethyl compound. Similar compositions are described, for example, in EP 445 624.

Further customary additives (d) are—depending upon the intended use—optical brighteners, fillers, pigments, both white and colored pigments, colorants, antistatics, wetting agents or flow improvers.

For curing thick and pigmented coatings it is suitable to add glass microbeads or pulverised glass fibers, as described e.g. in U.S. Pat. No. 5,013,768.

The formulations may also comprise colorants and/or white or colored pigments. Depending upon the intended use, both inorganic and organic pigments may be used. Such additives will be known to the person skilled in the art; some examples are titanium dioxide pigments, e.g. of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketo-pyrrolo-pyrrole, isoindolinone, e.g. tetrachloroisoindolinone, isoindoline, dioxazine, benzimidazolone and quinophthalone pigments. The pigments may be used in the formulations on their own or in admixture.

Depending upon the intended use, the pigments are added to the formulations in amounts customary in the art, for example in an amount of from 0.1 to 60% by weight, from 0.1 to 30% by weight or from 10 to 30.% by weight, based on the total mass.

The formulations may also comprise, for example, organic colorants of an extremely wide variety of classes. Examples are azo dyes, methine dyes, anthraquinone dyes and metal complex dyes. Customary concentrations are, for example, from 0.1 to 20%, especially from 1 to 5%, based on the total mass.

Depending upon the formulation used, it is also possible for compounds that neutralise acids, especially amines, to be used as stabilisers. Suitable systems are described, for example, in JP-A 11-199610. Examples are pyridine and derivatives thereof, N-alkyl- or N,N-dialkyl-anilines, pyrazine derivatives, pyrrole derivatives etc.

The choice of additives is governed by the field of use in question and the properties desired for that field. The additives (d) described above are customary in the art and are accordingly used in the amounts customary in the art.

The proportion of additional additives in the formulations according to the invention is, for example, from 0.01 to 10% by weight, for example from 0.05 to 5% by weight, especially from 0.1 to 5% by weight.

The invention relates also to compositions comprising as component (a) at least one ethylenically unsaturated photopolymerisable compound dissolved or emulsified in water.

Such aqueous radiation-curable prepolymer dispersions are commercially available in many variations and are to be understood as being dispersions consisting of water and at least one prepolymer dispersed therein. The concentration of water in such systems is, for example, from 2 to 80% by weight, especially from 30 to 60% by weight. The radiation-curable prepolymer or mixture of prepolymers is present, for example, in concentrations of from 95 to 20% by weight, especially from 70 to 40% by weight. In such compositions the sum of the percentages mentioned for water and prepolymer will be 100 in each case, the auxiliaries and additives, which will be present in varying amounts in accordance with the intended use, being in addition thereto.

The radiation-curable film-forming prepolymers, which are dispersed or in many cases dissolved in water, are monoor poly-functional ethylenically unsaturated prepolymers that can be initiated by free radicals, which prepolymers are known per se for aqueous prepolymer dispersions and contain, for example, from 0.01 to 1.0 mol of polymerisable double bonds per 100 g of prepolymer and have an average molecular weight of, for example, at least 400, especially of from 500 to 10 000. Prepolymers having higher molecular weights may also be suitable, however, depending upon the intended use.

There are used, for example, polymerisable C—C doublebond-containing polyesters having an acid number of a maximum of 10, polymerisable C—C double-bond-containing polyethers, hydroxyl-group-containing reaction products of a polyepoxide containing at least two epoxy groups per molecule with at least one $\alpha,\beta$-ethylenically unsaturated carboxylic acid, polyurethane (meth)acrylates and acrylic copolymers containing $\alpha,\beta$-ethylenically-unsaturated acrylic radicals, as described in EP 12 339. Mixtures of those prepolymers may also be used. Also suitable are the polymerisable prepolymers described in EP 33 896, which are thioether adducts of polymerisable prepolymers having an average molecular weight of at least 600, a carboxyl group content of from 0.2 to 15% and a content of from 0.01 to 0.8 mol of polymerisable C—C double bonds per 100 g of prepolymer. Other suitable aqueous dispersions based on specific (meth)acrylic acid alkyl ester polymerisation products are described in EP 41125, and suitable water-dispersible radiation-curable prepolymers of urethane acrylates can be found in DE 2 936 039.

As further additives, such radiation-curable aqueous prepolymer dispersions may comprise the additional additives (d) described above, that is to say e.g. dispersing agents, emulsifiers, anti-oxidants, light stabilisers, colorants, pigments, fillers, e.g. talcum, gypsum, silicic acid, rutile, carbon black, zinc oxide, iron oxides, reaction accelerators, flow agents, glidants, wetting agents, thickeners, dulling agents, antifoams and other adjuvants customary in surface-coating technology. Suitable dispersing agents include water-soluble high molecular weight organic compounds having polar groups, e.g. polyvinyl alcohols, polyvinylpyrrolidone and cellulose ethers. As emulsifiers it is possible to use non-ionic and, where appropriate, also ionic emulsifiers.

The photoinitiators of formula I according to the invention can also be dispersed as such in aqueous solutions and added in that dispersed form to the mixtures to be cured. When suitable non-ionic or, where applicable, ionic emulsifiers are added, the compounds of formula II or III according to the invention can be incorporated by mixing and e.g. grinding in water, forming stable emulsions which can be used as such as photoinitiators, especially for aqueous photocurable mixtures as described above.

In certain cases it may be advantageous to use mixtures of two or more of the photoiniators according to the invention. It is, of course, also possible to use mixtures with known photoinitiators, for example mixtures with camphorquinone, benzophenone, benzophenone derivatives, acetophenone, acetophenone derivatives, for example $\alpha$-hydroxycycloalkylphenyl ketones or 2-hydroxy-2-methyl-1-phenyl-propanone, dialkoxyacetophenones, $\alpha$-hydroxy- or $\alpha$-aminoacetophenones, e.g. (4-methylthiobenzoyl)-1-methyl-1-morpholino-ethane, (4-morpholino-benzoyl)-1-benzyl-1-dimethylamino-propane, 4-aroyl-1,3-dioxolanes, benzoin alkyl ethers and benzil ketals, e.g. benzil dimethyl ketal, phenyl glyoxalates and derivatives thereof, dimeric phenyl glyoxalates, peresters, e.g. benzophenonetetracarboxylic acid peresters, for example as described in EP 126 541, monoacylphosphine oxides, e.g. (2,4,6-trimethylbenzoyl)-phenyl-phosphine oxide, bisacylphosphine oxides, e.g. bis (2,6-dimethoxybenzoyl)-(2,4,4-trimethyl-pent-1-yl)-phosphine oxide, bis(2,4,6-trimethylbenzoyl)phenyl-phosphine oxide or bis(2,4,6-trimethylbenzoyl)-(2,4-dipentyloxyphenyl)phosphine oxide, trisacylphosphine oxides, halomethyltriazines, e.g. 2-[2-(4-methoxy-phenyl)-vinyl]-4,6-bis-trichloromethyl[1,3,5]triazine, 2-(4-methoxy-phenyl)-4,6-bis-trichloromethyl[1,3,5]triazine, 2-(3,4-dimethoxy-phenyl)-4,6-bis-trichloromethyl[1,3,5]triazine, 2-methyl-4, 6-bis-trichloromethyl[1,3,5]triazine, hexaarylbisimidazole/ coinitiator systems, e.g. ortho-chlorohexaphenyl-bisimidazole in combination with 2-mercaptobenzothiazole; ferrocenium compounds or titanocenes, for example dicyclopentadienyl-bis(2,6-difluoro-3-pyrrolo-phenyl)titanium;

O-acyloxime ester compounds as described e.g. in GB 2 339 571. As coinitiators it is also possible to use borate compounds.

When the photoinitiators according to the invention are used in hybrid systems (which in this connection mean mixtures of free-radically and cationically curing systems), in addition to the free-radical hardeners according to the invention there are also used cationic photoinitiators, e.g. benzoyl peroxide (other suitable peroxides are described in U.S. Pat. No. 4,950,581, column 19, lines 17–25), aromatic sulfonium, phosphonium or iodonium salts, as described e.g. in U.S. Pat. No. 4,950,581, column 18, line 60 to column 19, line 10, or cyclopentadienylarene-iron(II) complex salts, e.g. ($\eta^6$-isopropylbenzene)($\eta^5$-cyclopentadienyl) iron(II) hexafluorophosphate or photolatent acids based on oximes, as described, for example, in GB 2 348 644, U.S. Pat. Nos. 4,450,598, 4,136,055, WO 00/10972 and WO 00/26219.

The invention relates also to compositions wherein the additional photoiniators (c) are compounds of formula III, IV, V and/or VI

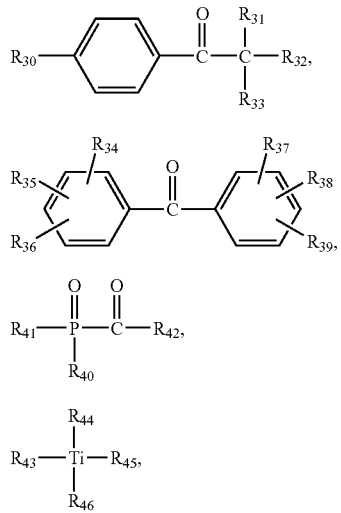

wherein
$R_{30}$ is hydrogen, $C_1$–$C_{18}$alkyl, $C_1$–$C_{18}$alkoxy, —OCH$_2$CH$_2$—OR$_{47}$, morpholino, SCH$_3$, a group

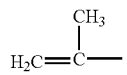

or a group

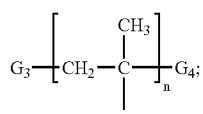

n has a value of from 2 to 10;
$G_3$ and $G_4$ are each independently of the other terminal groups of the polymeric unit, especially hydrogen or CH$_3$;
$R_{31}$ is hydroxy, $C_1$–$C_{16}$alkoxy, morpholino, dimethylamino or —O(CH$_2$CH$_2$O)$_m$—C$_1$–C$_{16}$alkyl;

$R_{32}$ and $R_{33}$ are each independently of the other hydrogen, $C_1$–$C_6$alkyl, phenyl, benzyl, $C_1$–$C_{16}$alkoxy or —O(CH$_2$CH$_2$O)$_m$—C$_1$–C$_{16}$alkyl, or $R_{32}$ and $R_{33}$ together with the carbon atom to which they are bonded form a cyclohexyl ring;

m is a number from 1 to 20;

wherein $R_{31}$, $R_{32}$ and $R_{33}$ are not all simultaneously $C_1$–$C_{16}$alkoxy or —O(CH$_2$CH$_2$O)$_m$—C$_1$–C$_{16}$alkyl;

$R_{47}$ is hydrogen,

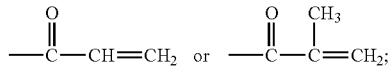

$R_{34}$, $R_{36}$, $R_{37}$ and $R_{38}$ are each independently of the others hydrogen or methyl;

$R_{35}$ and $R_{39}$ are hydrogen, methyl or phenylthio, the phenyl ring of the phenylthio radical being unsubstituted or substituted in the 4-, 2-, 2,4- or 2,4,6-position by $C_1$–$C_4$alkyl;

$R_{40}$ and $R_{41}$ are each independently of the other $C_1$–$C_{20}$alkyl, cyclohexyl, cyclopentyl, phenyl, naphthyl or biphenylyl, those radicals being unsubstituted or substituted by halogen, $C_1$–$C_{12}$-alkyl and/or $C_1$–$C_{12}$alkoxy, or $R_{40}$ and $R_{41}$ are a S- or N-containing 5- or 6-membered heterocyclic ring or —(CO)R$_{42}$;

$R_{42}$ is cyclohexyl, cyclopentyl, phenyl, naphthyl or biphenylyl, those radicals being unsubstituted or substituted by halogen, $C_1$–$C_4$alkyl and/or $C_1$–$C_4$alkoxy, or $R_{42}$ is a S- or N-containing 5- or 6-membered heterocyclic ring;

$R_{43}$ and $R_{44}$ are each independently of the other cyclopentadienyl unsubstituted or mono-, di- or tri-substituted by $C_1$–$C_{18}$alkyl, $C_1$–$C_{18}$alkoxy, cyclopentyl, cyclohexyl or halogen;

$R_{45}$ and $R_{46}$ are each independently of the other phenyl which is substituted by fluorine atoms or CF$_3$ in at least one of the two positions ortho to the titanium-carbon bond and may contain, as further substituents at the aromatic ring, polyoxaalkyl or pyrrolinyl unsubstituted or substituted by one or two $C_1$–$C_{12}$alkyl, di(C$_1$–C$_{12}$alkyl)aminomethyl, morpholinomethyl, $C_2$–$C_4$alkenyl, methoxymethyl, ethoxymethyl, trimethylsilyl, formyl, methoxy or phenyl substituents, or $R_{45}$ and $R_{46}$ are

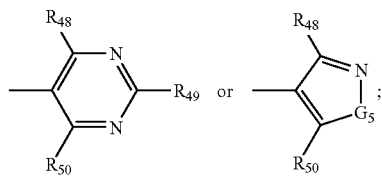

$R_{48}$, $R_{49}$ and $R_{50}$ are each independently of the others hydrogen, halogen, $C_2$–$C_{12}$alkenyl, $C_1$–$C_{12}$alkoxy, $C_2$–$C_{12}$alkoxy interrupted by from one to four O atoms, cyclohexyloxy, cyclopentyloxy, phenoxy, benzyloxy, or phenyl or biphenylyl each unsubstituted or substituted by $C_1$–$C_4$alkoxy, halogen, phenylthio or by $C_1$–$C_4$alkylthio, wherein $R_{48}$ and $R_{50}$ are not both simultaneously hydrogen and in the radical

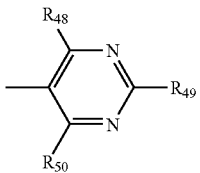

at least one radical $R_{48}$ or $R_{50}$ is $C_1$–$C_{12}$alkoxy, $C_2$–$C_{12}$alkoxy interrupted by from one to four O atoms, cyclohexyloxy, cyclopentyloxy, phenoxy or benzyloxy;

$G_5$ is O, S or $NR_{51}$; and $R_{51}$ is $C_1$–$C_8$alkyl, phenyl or cyclohexyl.

$R_{30}$ as $C_1$–$C_{18}$alkyl may have the same meanings as described for the compounds of formula I. $R_{32}$ and $R_{33}$ as $C_1$–$C_6$alkyl and $R_{31}$ as $C_1$–$C_4$alkyl may also have the same meanings as described above, up to the respective number of carbon atoms.

$C_1$–$C_{18}$Alkoxy is, for example, branched or unbranched alkoxy, e.g. methoxy, ethoxy, n-propoxy, isopropoxy, n-butoxy, isobutoxy, sec-butoxy, tert-butoxy, pentyloxy, hexyloxy, heptyloxy, octyloxy, 2,4,4-trimethyl-pent-1-yloxy, 2-ethylhexyloxy, nonyloxy, decyloxy, dodecyloxy or octadecyloxy.

$C_2$–$C_{12}$Alkoxy has the meanings given above up to the appropriate number of carbon atoms.

$C_1$–$C_{16}$Alkoxy has the same meanings as described above up to the appropriate number of carbon atoms, preference being given to decyloxy, methoxy and ethoxy, especially methoxy and ethoxy.

The radical —O($CH_2CH_2O$)$_m$—$C_1$–$C_{16}$alkyl denotes from 1 to 20 consecutive ethylene oxide units the chain of which is terminated by a $C_1$–$C_{16}$alkyl group. Preferably m is from 1 to 10, e.g. from 1 to 8, especially from 1 to 6. The ethylene oxide unit chain is preferably terminated by a $C_1$–$C_{10}$alkyl group, e.g. by a $C_1$–$C_8$alkyl group, especially by a $C_1$–$C_4$alkyl group. $R_{35}$ as a substituted phenylthio ring is preferably p-tolylthio.

$R_{40}$ and $R_{41}$ as $C_1$–$C_{20}$alkyl are linear or branched and are, for example, $C_1$–$C_{12}$-, $C_1$–$C_8$-, $C_1$–$C_6$- or $C_1$–$C_4$-alkyl. Examples are as indicated above. $R_{40}$ as alkyl is preferably $C_1$–$C_8$alkyl.

$R_{40}$, $R_{41}$ and $R_{42}$ as substituted phenyl are mono- to penta-substituted, e.g. mono-, di- or tri-substituted, especially tri- or di-substituted, on the phenyl ring. Substituted phenyl, naphthyl or biphenylyl are substituted e.g. by linear or branched $C_1$–$C_4$alkyl, such as methyl, ethyl, n-propyl, isopropyl, n-butyl, isobutyl, sec-butyl or tert-butyl, or by linear or branched $C_1$–$C_4$alkoxy, such as methoxy, ethoxy, n-propoxy, isopropoxy, n-butoxy, isobutoxy, sec-butoxy or tert-butoxy, preferably by methyl or methoxy.

When $R_{40}$, $R_{41}$ and $R_{42}$ are a S- or N-containing 5- or 6-membered heterocyclic ring, they are, for example, thienyl, pyrrolyl or pyridyl.

In the term di($C_1$–$C_{12}$alkyl)aminomethyl, $C_1$–$C_{12}$alkyl has the same meanings as indicated above.

$C_2$–$C_{12}$Alkenyl is linear or branched, may be mono- or poly-unsaturated and is, for example, allyl, methallyl, 1,1-dimethylallyl, 1-butenyl, 2-butenyl, 1,3-pentadienyl, 1-hexenyl or 1-octenyl, especially allyl.

$C_1$–$C_4$Alkylthio is linear or branched and is, for example, methylthio, ethylthio, n-propylthio, isopropylthio, n-butylthio, isobutylthio, sec-butylthio or tert-butylthio, preferably methylthio.

$C_2$–$C_4$Alkenyl is, for example, allyl, methallyl, 1-butenyl or 2-butenyl.

Halogen is fluorine, chlorine, bromine or iodine, preferably fluorine, chlorine or bromine.

The term polyoxaalkyl includes $C_2$–$C_{20}$alkyl interrupted by from 1 to 9 O atoms and denotes e.g. structural units such as $CH_3$—O—$CH_2$—, $CH_3CH_2$—O—$CH_2CH_2$—, $CH_3O$[$CH_2CH_2O$]$_y$— wherein y=1–9, —($CH_2CH_2O$)$_7CH_2CH_3$ and —$CH_2$—$CH(CH_3)$—O—$CH_2$—$CH_2CH_3$.

Preference is given to compositions wherein $R_{30}$ is hydrogen, —$OCH_2CH_2$—$OR_{47}$, morpholino, $SCH_3$, a group

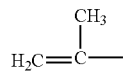

or a group

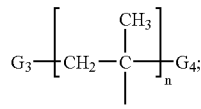

$R_{31}$ is hydroxy, $C_1$–$C_{16}$alkoxy, morpholino or dimethylamino;

$R_{32}$ and $R_{33}$ are each independently of the other $C_1$–$C_4$alkyl, phenyl, benzyl or $C_1$–$C_{16}$alkoxy, or $R_{32}$ and $R_{33}$ together with the carbon atom to which they are bonded form a cyclohexyl ring;

$R_{47}$ is hydrogen or

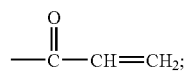

$R_{34}$, $R_{35}$ and $R_{36}$ and $R_{37}$, $R_{38}$ and $R_{39}$ are hydrogen or $C_1$–$C_4$alkyl;

$R_{40}$ is $C_1$–$C_{12}$alkyl, unsubstituted phenyl, or phenyl substituted by $C_1$–$C_{12}$alkyl and/or $C_1$–$C_{12}$alkoxy;

$R_{41}$ is (CO)$R_{42}$; and $R_{42}$ is phenyl which is substituted by $C_1$–$C_4$alkyl and/or $C_1$–$C_4$alkoxy.

Preferred compounds of formulae III, IV, V and VI are α-hydroxycyclohexyl phenyl ketone or 2-hydroxy-2-methyl-1-phenyl-propanone, (4-methylthiobenzoyl)-1-methyl-1-morpholinoethane, (4-morpholino-benzoyl)-1-benzyl-1-dimethylamino-propane, benzil dimethyl ketal, (2,4,6-trimethylbenzoyl)-phenyl-phosphine oxide, bis(2,6-dimethoxybenzoyl)-(2,4,4-trimethylpent-1-yl)phosphine oxide, bis(2,4,6-trimethylbenzoyl)-phenyl-phosphine oxide or bis(2,4,6-trimethylbenzoyl)-(2,4-dipentyloxyphenyl) phosphine oxide and dicyclopentadienyl-bis(2,6-difluoro-3-pyrrolo)titanium.

Also preferred are compositions wherein in formula III $R_{32}$ and $R_{33}$ are each independently of the other $C_1$–$C_6$alkyl, or together with the carbon atom to which they are bonded form a cyclohexyl ring and $R_{31}$ is hydroxy.

The proportion of compounds of formula I (=photoinitiator component (b)) in admixture with compounds of formulae III, IV, V and/or VI (=photoinitiator component (c)) is from 5 to 99%, e.g. 20–80%, preferably from 25 to 75%.

Also important are compositions wherein in the compounds of formula III $R_{32}$ and $R_{33}$ are identical and are methyl and $R_{31}$ is hydroxy or isopropoxy.

Preference is likewise given to compositions comprising compounds of formula I and compounds of formula V wherein $R_{40}$ is phenyl unsubstituted or substituted by from one to three $C_1$–$C_{12}$alkyl and/or $C_1$–$C_{12}$alkoxy substituents or is $C_1$–$C_{12}$alkyl;

$R_{41}$ is a group (CO)$R_{42}$ or phenyl; and $R_{42}$ is phenyl substituted by from one to three $C_1$–$C_4$alkyl or $C_1$–$C_4$alkoxy substituents.

Of very special interest are compositions as described above that comprise photoinitiator mixtures of formulae I, III, IV, V and/or VI and are liquid at room temperature.

The preparation of compounds of formulae III, IV, V and VI is generally known to the person skilled in the art and some of the compounds are commercially available. The preparation of oligomeric compounds of formula III is described, for example, in EP 161 463. A description of the preparation of compounds of formula IV can be found e.g. in EP 209 831. The preparation of compounds of formula V is disclosed e.g. in EP 7508, EP 184 095 and GB 2 259 704. The preparation of compounds of formula VI is described e.g. in EP 318 894, EP 318 893 and EP 565 488.

The photopolymerisable compositions comprise the photoinitiator advantageously in an amount of from 0.05 to 20% by weight, e.g. from 0.05 to 15% by weight, preferably from 0.1 to 5% by weight, based on the composition. The amount of photoinitiator indicated relates to the sum of all added photoinitiators when mixtures thereof are used, that is to say both to the photoinitiator (b) and to the photoinitiators (b)+(c).

Compounds according to the invention wherein X is a siloxane-containing radical are especially suitable as photoinitiators for surface coatings, especially automotive finishes. Such photoinitiators are not distributed in the formulation to be cured as homogeneously as possible, but are concentrated selectively at the surface of the coating to be cured; that is to say the initiator is selectively oriented towards the surface of the formulation.

The photopolymerisable compositions may be used for a variety of purposes, for example as printing inks, such as screen printing inks, flexographic printing inks and offset printing inks, as clearcoats, as colored coats, as whitecoats, for example for wood or metal, as powder coatings, as coating materials inter alia for paper, wood, metal or plastics, as daylight-curable paints for marking structures and roads, for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as photoresists, e.g. galvanoresists, as etch resists or permanent resists, both liquid and dry films, as photostructurable dielectrics, and as solder masks for electronic circuits, as resists in the production of color filters for any type of display screen or in the creation of structures during the manufacture of plasma displays and electroluminescent displays, in the production of optical switches, optical gratings (interference gratings), in the manufacture of three-dimensional articles by bulk curing (UV curing in transparent moulds) or according to the stereolithography process, as described, for example, in U.S. Pat. No. 4,575,330, in the manufacture of composite materials (e.g. styrene polyesters which may include glass fibers and/or other fibers and other adjuvants) and other thick-layered compositions, in the coating or sealing of electronic components or as coatings for optical fibers. The compositions are also suitable for the production of optical lenses, e.g. contact lenses or Fresnel lenses, and also in the manufacture of medical apparatus, aids or implants.

The compositions are also suitable for the preparation of gels having thermotropic properties. Such gels are described e.g. in DE 197 00 064 and EP 678 534.

The compositions can also be used in dry film paints, as described e.g. in Paint & Coatings Industry, April 1997, 72 or Plastics World, Vol. 54, No. 7, page 48(5).

The compounds according to the invention may also be used as initiators for emulsion, bead or suspension polymerisation or as initiators of a polymerisation step for fixing orientation states of liquid-crystalline monomers and oligomers or as initiators for fixing dyes on organic materials.

In surface coatings, use is frequently made of mixtures of a prepolymer with polyunsaturated monomers that also comprise a monounsaturated monomer, the prepolymer in particular determining the properties of the surface-coating film, so that a person skilled in the art will be able to influence the properties of the cured film by varying the prepolymer. The polyunsaturated monomer functions as a crosslinking agent, which renders the surface-coating film insoluble. The monounsaturated monomer functions as a reactive diluent, by means of which the viscosity is reduced without the need to use a solvent.

Unsaturated polyester resins are generally used in two-component systems together with a monounsaturated monomer, preferably styrene. For photoresists, specific one-component systems are often used, e.g. polymaleinimides, polychalcones or polyimides, as described in DE 2 308 830.

The compounds and mixtures thereof according to the invention may also be used as free-radical photoinitiators or photoinitiating systems for radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (e.g. methylacrylamidoglycolate methyl ester) and a free-radical photoinitiator according to the invention, as described, for example, in the presentation "Radiation Curing of Powder Coating", Conference Proceedings, Radtech Europe 1993 by M. Wittig and Th. Gohmann. Similarly, free-radically UV-curable powder coatings can be formulated by mixing unsaturated polyester resins with solid acrylates, methacrylates or vinyl ethers and a photoinitiator (or photoinitiator mixture) according to the invention. The powder coatings may also comprise binders, as described, for example, in DE 4 228 514 and EP 636 669. The UV-curable powder coatings may also comprise white or colored pigments. For example, especially rutile/titanium dioxide may be used in concentrations of up to approximately 50% by weight in order to obtain a cured powder coating having good hiding power. The process normally comprises spraying the powder electrostatically or tribostatically onto the substrate, for example metal or wood, melting the powder by heating and, after a smooth film has formed, radiation-curing the coating with ultraviolet and/or visible light, for example using medium-pressure mercury lamps, metal halide lamps or xenon lamps. A particular advantage of radiation-curable powder coatings over corresponding thermally curable coatings is that the flow time after the powder particles have been melted can be prolonged as desired in order to ensure the formation of a smooth high-gloss coating. Unlike thermally curable systems, radiation-curable powder coatings can be so formulated that they melt at relatively low temperatures without the undesired effect of their useful life being shortened. For that reason they are also suitable as coatings for heat-sensitive substrates, such as wood or plastics.

In addition to the photoinitiators according to the invention the powder coating formulations may also comprise UV absorbers. Appropriate examples are listed hereinabove under points 1 to 8.

The photocurable compositions according to the invention are suitable, for example, as coating materials for all kinds of substrate, for example wood, textiles, paper, ceramics, glass, plastics, such as polyesters, polyethylene terephthalate, polyolefins and cellulose acetate, especially in the form of films, and also metals, such as Al, Cu, Ni, Fe, Zn, Mg or Co and GaAs, Si or $SiO_2$, to which a protective layer is to be applied or an image is to be applied e.g. by imagewise exposure.

The substrates can be coated by applying a liquid composition, a solution or a suspension to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents include, for example, ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating methods, for example by spin-coating, immersion, knife coating, curtain pouring, brush application or spraying, especially e.g. by electrostatic spraying and reverse-roll coating, and also by electrophoretic deposition. It is also possible to apply the photosensitive layer to a temporary flexible support and then coat the final substrate, e.g. a copper-clad circuit board, by transferring the layer via lamination.

The amount applied (layer thickness) and the nature of the substrate (layer support) are dependent upon the desired field of application. The person skilled in the art will be familiar with the layer thicknesses suitable for the field of application in question, for example in the field of photoresists, printing inks or paints. The range of layer thicknesses generally includes values from about 0.1 µm to more than 10 mm, depending upon the field of application.

The radiation-sensitive compositions according to the invention are used, for example, as negative resists that have a very high degree of photosensitivity and can be developed in an aqueous-alkaline medium without swelling. They are suitable as photoresists for electronics, such as galvanoresists, etch resists, in both liquid and dry films, as solder resists, as resists in the production of color filters for any type of display screen, or in the formation of structures during the manufacture of plasma displays and electroluminescent displays, for the production of printing plates, such as offset printing plates, for the manufacture of printing blocks for letterpress printing, planographic printing, intaglio printing, flexographic printing or screen printing blocks, for the preparation of relief copies, e.g. for the preparation of texts in braille, for the production of dies, for use in the etching of mouldings or for use as microresists in the production of integrated circuits. The compositions can also be used as photostructurable dielectrics, for the encapsulation of materials or as insulator coating for the production of computer chips, printed circuits and other electrical or electronic components. The layer supports that are possible and the conditions for processing the coated substrates are correspondingly various.

The compounds according to the invention are also used in the production of single- or multilayer materials for image recording or image duplication (copying, reprographics), which may be monochrome or polychrome. Those materials can also be used in color-testing systems. In that technology it is also possible to use formulations containing microcapsules, and for creating the image the exposure step can be followed by a thermal step. Such systems and technologies and their use are described e.g. in U.S. Pat. No. 5,376,459.

For photographic information recordings there are used, for example, foils of polyester, cellulose acetate or plastics-coated papers; for offset printing blocks e.g. specially treated aluminium, for the production of printed circuits e.g. copper-clad laminates, and for the production of integrated circuits on silicon wafers. The customary layer thicknesses for photographic materials and offset printing blocks are generally about from 0.5 µm to 10 µm, and for printed circuits from 1.0 µm to about 100 µm.

After the substrates have been coated, the solvent is generally removed by drying, resulting in a layer of photoresist on the support.

The term "imagewise" exposure includes both exposure using a photomask having a predetermined pattern, e.g. a transparency, exposure using a laser beam which is moved over the surface of the coated substrate, for example under computer control, and in that way produces an image, and irradiation with computer-controlled electron beams. It is also possible to use masks of liquid crystals which can be actuated pixel by pixel in order to create digital images, as described e.g. by A. Bertsch, J. Y. Jezequel, J. C. Andre in Journal of Photochemistry and Photobiology A: Chemistry 1997, 107, pp. 275–281 and by K.-P. Nicolay in Offset Printing 1997, 6, pp. 34–37.

Conjugated polymers, e.g. polyanilines, can be converted from a semi-conductive state to a conductive state by doping with protons. The photoinitiators according to the invention can also be used for the imagewise exposure of polymer compositions comprising such polymers in order to form conductive structures (in the irradiated zones) which are embedded in insulating material (non-exposed zones). Such materials can be used, for example, as wiring components or connecting components for the production of electrical or electronic components.

After the imagewise exposure of the material and prior to development it may be advantageous to carry out a thermal treatment for a relatively short time. During the thermal treatment only the exposed areas are thermally cured. The temperatures used are generally from 50 to 150° C., preferably from 80 to 130° C.; the duration of the thermal treatment is generally from 0.25 to 10 minutes.

The photocurable composition may also be used in a method of producing printing blocks or photoresists, as described e.g. in DE 4 013 358. In such a method, before, at the same time as or after the imagewise irradiation the composition is, without a mask, exposed briefly to visible light of a wavelength of at least 400 nm. After the exposure and optional thermal treatment, the unexposed areas of the photosensitive coating are removed using a developer in a manner known per se.

As already mentioned, the compositions according to the invention can be developed in an aqueous-alkaline medium. Suitable aqueous-alkaline developer solutions are especially aqueous solutions of tetraalkylammonium hydroxides or of alkali metal silicates, phosphates, hydroxides and carbonates. If desired, relatively small amounts of wetting agents and/or organic solvents may be added to those solutions. Typical organic solvents that may be added in small amounts to the developer fluids are, for example, cyclohexanone, 2-ethoxyethanol, toluene, acetone and mixtures of such solvents.

Photocuring is of great importance for printing inks, since the drying time of the binder is a determining factor in the rate of production of graphic products and should be of the order of fractions of a second. UV-curable inks are important especially for screen printing, flexographic printing and offset printing.

As already mentioned above, the mixtures according to the invention are also very suitable for the production of printing plates. For that application there are used, for example, mixtures of soluble linear polyamides or styrene/butadiene or styrene/isoprene caoutchouc, polyacrylates or polymethyl methacrylates having carboxyl groups, polyvinyl alcohols or urethane acrylates with photopolymerisable monomers, for example acrylic or methacrylic amides or acrylic or methacrylic esters, and a photoinitiator. Films and plates made from those systems (wet or dry) are exposed through the negative (or positive) of the original and the uncured portions are then eluted with a suitable solvent.

Another field of use for photocuring is metal coating, for example in the application of a finish to sheets and tubes, cans or bottle closures, as well as photocuring on plastics coatings, for example of PVC-based floor or wall coverings. Examples of the photocuring of paper coatings include the application of a colorless finish to labels, record sleeves or book covers.

Also of interest is the use of the compounds according to the invention in the curing of mouldings made of composite materials. The composite material consists of a self-supporting matrix material, for example woven glass fibers, or alternatively, for example, plant fibers [see K.-P. Mieck, T. Reussmann in Kunststoffe 85 (1995), 366–370], which is impregnated with the photocuring formulation. Mouldings of composite materials made using the compounds according to the invention achieve a high degree of mechanical stability and resistance. The compounds according to the invention can also be used as photohardeners in moulding, impregnating and coating materials, as described, for example, in EP 7086. Such materials are, for example, thin-layer resins, on which high demands are made in terms of curing activity and resistance to yellowing, and fiber-reinforced moulding materials, such as planar or longitudinally or transversely corrugated light panels. Processes for the production of such moulding materials, such as, for example, manual lay-up processes, fiber-spraying, spinning or winding processes, are described, for example, by P. H. Selden in "Glasfaserverstärkte Kunststoffe", page 610, Springer Verlag Berlin-Heidelberg-New York 1967. Articles that can be produced, for example, according to that process are boats; chipboard or plywood panels coated on both sides with glass-fiber-reinforced plastics; pipes; sports equipment; roof coverings; containers etc. Further examples of moulding, impregnating and coating materials are UP resin thin layers for glass-fiber-containing moulding materials (GRP), for example corrugated panels and paper laminates. Paper laminates may be based on urea or melamine resins. The thin layer is produced on a support (for example a foil) prior to production of the laminate. The photocurable compositions according to the invention may also be used for casting-resins or for the potting of articles, for example electronic components etc. They may also be used for lining cavities and pipes. For curing, medium pressure mercury vapour lamps are used, as are customary in UV curing, but less intense lamps, for example of the TL 40W/03 or TL40W/05 type, are also of particular interest. The intensity of those lamps roughly corresponds to that of sunlight. Direct sunlight can also be used for curing. A further advantage is that the composite material can be removed from the light source in a partially cured, plastic state and subjected to shaping, after which the full cure is effected.

The photoinitiators according to present invention are also suitable for use in compositions as coatings for optical fibers. In general, optical fibers are coated with protective coats directly after their production. The fiber of glass is drawn and then one or more coatings are applied to the glass string. Usually, one, two or three coats are applied, the top coating, for example, is colored ("ink layer or ink coating"). Further, several thus coated optical fibers may be put together to a bundle and be coated all together, i.e. cabling of the fibers. The compositions according to the present invention in general are suitable for any of these coatings, which have to exhibit good softness over a broad temperature range, good tensile strength and toughness and rapid UV-curing characteristics.

Each of the coats, inner primary (usually a soft coating), outer primary or secondary (usually a harder coating than the inner coating), tertiary or the cabling coat, may comprise at least one radiation-curable oligomer, at least one radiation curable monomer diluent, at least one photoinitiator, and additives.

In general all radiation curable oligomers are suitable. Preferred are oligomers with a molecular weight of at least 500, for example 500–10 000, 700–10 000, 1000–8000 or 1000–7000, in particular urethane oligomers, containing at least one unsaturated group. Preferably the radiation curable oligomer has two terminal functional groups. The coat may contain not only one specific oligomer, but also mixtures of different oligomers. The preparation of suitable oligomers is known to the person skilled in the art and for example published in U.S. Pat. No. 6,136,880, incorporated herein by reference. The oligomers are, for example, prepared by reacting an oligomer diol, preferably a diol having 2–10 polyoxaalkylene groups, with a diisocyanate or a polyisocyanate and a hydroxy-functional ethylenically unsaturated monomer, e.g. hydroxyalkyl(meth)acrylate. Specific examples of each of the components named above, as well as suitable ratios of these components are given in U.S. Pat. No. 6,136,880, incorporated herein by reference.

The radiation curable monomer can be used in a manner to control the viscosity of the coating formulation. Accordingly, a low viscosity monomer with at least one functional group capable of photoinitiated polymerization is employed. The amount for example is chosen to adjust the viscosity in a range from 1000 to 10 000 mPas, i.e. usually for example from 10–90, or 10–80% by weight are used. The functional group of the monomer diluent preferably is of the same kind as the one of the oligomer component, for example an acrylate or vinyl ether function and a higher alkyl or polyether moiety. Examples of monomer diluents suitable for coating compositions for optical fibers are published in U.S. Pat. No. 6,136,880, col. 12, line 11ff., incorporated herein by reference.

In primary coatings preferably monomers having an acrylate or vinyl ether functionality and a polyether moiety of 4 to 20 C atoms is used. Specific examples are given in the US patent incorporated by reference and cited above.

The composition may also comprise a poly(siloxane) as described in U.S. Pat. No. 5,595,820 to improve the adhesive properties of the formulation on the optical fiber glass substrate.

The coating composition usually also comprises further additives, e.g. antioxidants, light stabilizers, UV absorbers such as for example given in the list above, in particular ®ANOX 1035, 1010, 1076, 1222, ®TINUVIN P, 234, 320, 326, 327, 328, 329, 213, 292, 144, 622LD (all provided by Ciba Specialty Chemicals), ®ANTIGENE P, 3C, FR, GA-80, ®SUMISORB TM-061 (provided by Sumitomo Chemical Industries Co.), ®SEESORB 102, 103, 501, 202, 712, 704 (provided by Sypro Chemical Co., Ltd.), ®SANOL LS770 (provided by Sankyo Co. Ltd.) to prevent the coloring of the coat, in particular during the processing, and to improve the stability of the cured coat. Particularly interesting are stabilizer combinations of hindered piperidine derivatives (HALS) and hindered phenol compounds, e.g. a combination of IRGANOX 1035 and TINUVIN 292, for example in a ratio of 1:1. Further, additives are for example wetting agents and other additives having an effect on the rheology properties of the coating. Also amines, for example diethylamine, can be added. Other examples for additives for compositions for the coating of optical fibers are silane coupling agents, e.g. γ-aminopropyltriethoxysilane, γ-mercaptopropyltrimethoxysilane, γ-methacryloxypropyl-trimethoxysilane, SH6062, SH6030 (provided by Toray-Dow Corning Silcone Co., Ltd.), KBE 903, KBE 603, KBE 403 (provided by Shin-Etsu Chemical Co., Ltd.) In order to prevent coloring of the coatings the compositions may also comprise fluorescent additives or optical brighteners, as, for example, ®UVITEX OB, provided by Ciba Specialty Chemicals.

The photoinitiators according to the present application in coating compositions for optical fibers can be admixed with one or more other known photoinitiators. These are in particular monoacylphosphine oxides, such as diphenyl-2,4,6-trimethylbenzoyl phosphine oxide; bisacylphosphine oxides, such as bis(2,4,6-trimethylbenzoyl)-phenyl phosphine oxide (®IRGACURE 819), bis(2,6-dimethoxybenzoyl)-2,4,4-trimethylpentyl phosphine oxide; α-hydroxyketones, such as 1-hydroxycyclohexyl phenyl ketone (®IRGACURE 184), 2-hydroxy-2-methyl-1-phenyl-1-propanone (®DAROCUR 1173), 2-hydroxy-1-[4-(2-hydroxyethoxy)phenyl]-2-methyl-1-propanone (®IRGACURE 2959); α-aminoketones, such as 2-methyl-1-[4-(methylthio) phenyl]-2-(4-morpholinyl)-1-propanone (®IRGACURE 907), 2-benzyl-2-(dimethylamino)-1-[4-(4-morpholinyl) phenyl]-1-butanone (®IRGACURE 369); benzophenones, such as benzophenone, 2,4,6-trimethylbenzophenone, 4-methylbenzophenone, 2-methylbenzophenone, 2-methoxycarbonylbenzophenone, 4,4'-bis(chloromethyl)benzophenone, 4-chlorobenzophenone, 4-phenylbenzophenone, 4,4'-bis (dimethylamino)benzophenone, 4,4'-bis(diethylamino)benzophenone, methyl 2-benzoylbenzoate, 3,3'-dimethyl-methoxybenzophenone, 4-(4-methylphenylthio) benzophenone and also ketal compounds, for example 2,2-dimethoxy-1,2-diphenyl-ethanone (®IRGACURE 651); monomeric or dimeric phenylglyoxalic acid esters, such as for example methyl phenylglyoxalic acid ester or 1,2-(benzoylcarboxy)ethane. In particular suitable are admixtures with mono- or bis-acylphosphine oxides and/or α-hydroxy ketones.

It is evident that the formulations, in order to enhance the properties of the photoinitiators may also comprise sensitizer compounds, for example amines.

The coatings are either applied "wet on dry" or "wet on wet". In the first case after the application of the primary coat a curing step by irradiation with UV light is carried out prior to the application of the second coat. In the second case both coatings are applied and cured together by irradiation with UV light.

The curing with UV irradiation in this application usually takes place in a nitrogen atmosphere. In general all radiation sources usually employed in the photocuring technique can be used for the curing of optical fiber coatings. These are, for example the radiation sources listed below. Generally, mercury medium pressure lamps or/and Fusion D lamps are used. Also flash lights are suitable. It is evident that the emission of the lamps is matched with the absorption of the photoinitiator or photoinitiator mixture which is used. The optical fiber coating compositions may also be cured by irradiation with an electron beam, in particular with low power electron beams, as is, for example, disclosed in WO 98/41484.

In order to distinguish different fibers in an assembly, the fibers may be covered with a third colored coating ("ink coating"). The compositions used for this coating in addition to the polymerizable components and the photoinitiator comprise a pigment or dye. Examples for pigments suitable for optical fiber coatings are inorganic pigments, such as for example titanium dioxide, zinc oxide, zinc sulfide, barium sulfate, aluminium silicate, calcium silicate, carbon black, black iron oxide, copper chromite black, iron oxides, chromium oxide greens, iron blue, chrome green, violet (e.g. manganese violet, cobalt phosphate, $CoLiPO_4$), lead chromates, lead molybdates, cadmium titanate and pearlescent and metallic pigments, as well as organic pigments, such as monoazo pigments, di-azo pigments, di-azo condensation pigments, quinacridone pigments, dioxazine violet, vat pigments, perylene pigments, thioindigo pigments, phthalocyanine pigments and tetrachloroisoindolinones. Examples for suitable pigments are carbon black for a black coating, titanium dioxide for a white coating, diarylide yellow or diazo based pigments for yellow coatings, phthalocyanine blue, and other phthalocyanines for blue coatings, anthraquinone red, naphthole red, monazo based pigments, quinacridone pigments, anthraquinone and perylenes for red coatings, phthalocyanine green and nitroso based pigments for green coatings, monazo and diazo based pigments, quinacridone pigments, anthraquinones and perylenes for orange coatings, and quinacridone violet, basic dye pigments and carbazole dioxazine based pigments for violet coatings. The person skilled in the art is well aware of formulating and combining suitable further pigments if even more colored coatings, such as aqua, brown, gray, pink etc. are needed. The mean particle size of the pigments usually is about 1 μm or less. The size of commercial pigments can be reduced by milling, if necessary. The pigments for example, can be added to the formulation in the form of a dispersion in order to simplify the mixing with the other ingredients of the formulation. The pigments are, for example dispersed in a low viscosity liquid, e.g. a reactive diluent. Preferred is the use of organic pigments. Suitable amounts for pigment in the ink coating are for example 1–20, 1–15, preferably 1–10% by weight.

The ink coating in general also comprises a lubricant to provide improved break-out properties of the single coated optical fiber from the matrix. Examples of such lubricants are silicones, fluorocarbon oils or resins and the like, preferably a silicone oil or a functionalized silicone compound, e.g. silicone diacrylate is used.

The compositions according to the present invention are further suitable as a matrix material for an assembly of coated optical fibers. That is, several of the primary, secondary (and in some cases tertiary) coated fibers, for example, in the third coat being differentiated by different colors, are assembled in a matrix.

The coating of an assembly preferably besides the additives given above also contains a release agent to allow for easy access to the individual fibers during the installation of the optical fiber cables. I.e.

Examples for such release agents are teflon, silicones, silicon acrylates, fluorocarbon oils or resins and the like. The release agents suitably are added in an amount of 0.5–20 wt %. Examples of ink coatings and matrix materials for coated optical fibers are given in U.S. Pat. Nos. 6,197,422, 6,130,980 and EP 614 099, incorporated herein by reference.

The compositions and compounds according to the invention can also be used in the production of light waveguides and optical switches, wherein the production of a difference in refractive index between exposed and non-exposed regions is utilised.

Also important is the use of photocurable compositions for imaging processes and for the optical production of information carriers. For that application, as already described above, the layer (wet or dry) applied to the support is irradiated with UV or visible light using a photomask and the unexposed areas of the layer are removed by treatment with a solvent (=developer). The photocurable layer can also be applied to metal in an electrodeposition process. The exposed areas are crosslinked-polymeric and are therefore insoluble and remain on the support. When suitably colored, visible images are formed. When the support is a metallised layer, after exposure and development the metal can be etched away in the unexposed areas or strengthened by galvanisation. In this way it is possible to produce printed electronic circuits and photoresists.

The photosensitivity of the compositions according to the invention usually extends from approximately 200 nm to approximately 600 nm (UV field). Suitable radiation is present, for example, in sunlight or light from artificial light sources. Accordingly a large number of the most varied kinds of light source may be used. Both point sources and planiform radiators (lamp carpets) are suitable. Examples are: carbon arc lamps, xenon arc lamps, medium pressure, high pressure and low pressure mercury arc radiators, doped, where appropriate, with metal halides (metal halide lamps), microwave-excited metal vapour lamps, excimer lamps, superactinic fluorescent tubes, fluorescent lamps, argon incandescent lamps, flash lamps, photographic floodlight lamps, light-emitting diodes (LED), electron beams and X-rays. The distance between the lamp and the substrate according to the invention to be exposed may vary according to the intended use and the type and strength of the lamp and may be, for example, from 2 cm to 150 cm. Especially suitable are laser light sources, for example excimer lasers, such as Krypton-F lasers e.g. for exposure at 248 nm. Lasers in the visible range may also be used. According to this method it is possible to produce printed circuits in the electronics industry, lithographic offset printing plates or relief printing plates and also photographic image-recording materials.

The invention therefore relates also to a process for the photopolymerisation of non-volatile monomeric, oligomeric or polymeric compounds having at least one ethylenically unsaturated double bond, wherein a composition as described above is irradiated with light in a range of from 200 to 600 nm. The invention relates also to the use of the compounds of formula I as photoinitiators for the photopolymerisation of non-volatile monomeric, oligomeric or polymeric compounds having at least one ethylenically unsaturated double bond by irradiation with light in a range of from 200 to 600 nm The invention relates also to the use of the above-described composition or a process for the preparation of pigmented and non-pigmented surface coatings, printing inks, e.g. screen-printing inks, offset printing inks, flexographic printing inks, powder coatings, printing plates, adhesives, dental compounds, light waveguides, optical switches, color-testing systems, bonding compounds, glass fiber cable coatings, screen-printing stencils, resist materials, color filters, their use for encapsulating electrical and electronic components, for the production of magnetic recording materials, for the production of three-dimensional articles by means of stereolithography, for photographic reproductions, and their use as image-recording material, especially for holographic recordings, for decolorising materials, for decolorising materials for image-recording materials, and for image-recording materials using microcapsules.

The invention relates also to a coated substrate which is coated on at least one surface with a composition as described above, and to a process for the photographic production of relief images in which a coated substrate is exposed imagewise and then the unexposed portions are removed with a solvent. The imagewise exposure can be effected through a mask or by means of laser beam, exposure by means of a laser beam being of special interest.

The bisacylphosphine oxides according to the invention, by virtue of their particular substitution, exhibit a marked bathochromic shift of the absorption spectrum. They are therefore suitable also as photoinitiators in a wavelength range above 400 nm. The compounds according to the invention are suitable as photoinitiators for curing strongly pigmented layers, dark-pigmented layers, very thick layers, gel-coats and bonding compounds. They can also be used for adhesively bonding materials, e.g. films, that absorb a high proportion of light below 400 nm, e.g. polycarbonate materials. The compounds according to the invention are especially suitable as photoinitiators when cured using lamps that emit a low proportion of UV light. This is of interest e.g. in the curing of dental fillings made of pigmented resin formulations or of repair coatings, e.g. automotive repair coatings, without the expensive installation of UV irradiation apparatus. The initiators according to the invention are also suitable for curing with daylight.

The following Examples illustrate the invention further. As in the rest of the description and in the patent claims, parts or percentages relate to weight unless otherwise indicated. Where reference is made to alkyl or alkoxy radicals having more than three carbon atoms without any indication of their isomeric form, the respective n-isomers are intended.

Preparation of Phosphines

EXAMPLE 1

Preparation of
4-[bis(2-methoxy-ethyl)amino]-phenyl-phosphine 78.4 g (0.37 mol) of 4-[bis(2-methoxy-ethyl)amino]-benzene and 0.5 g (0.0037 mol) of zinc chloride are introduced into 203.3 g (1.48 mol) of phosphorus trichloride and heated to 80–90° C. After stirring overnight, the excess phosphorus trichloride is removed from the reaction suspension by distillation. The residue is taken up in a small amount of toluene and clarified by filtration through a filtration aid (Hyflo) and then concentrated using a rotary evaporator. The phosphorus dichloride is obtained as intermediate for the title compound in the form of a clear orange oil ($^{31}$P-NMR: 164.9 ppm). For the synthesis of the title compound, 78 g (0.263 mol) of that intermediate are slowly added dropwise under argon at 0° C. to a suspension of 20.0 g (0.527 mol) of lithium aluminium hydride in 600 ml of tetrahydrofuran. After stirring at room temperature overnight to complete the reaction there are slowly added dropwise at 0° C. 20 g of water, followed by 20 g of 10% sodium hydroxide solution and a further 60 g of water. The white reaction suspension is filtered with suction under argon and the mother liquor is concentrated using a rotary evaporator. After distillation under a high vacuum (b.p. 123° C./0.0654 mbar) the title compound is obtained in the form of a clear colorless oil ($^{31}$P-NMR: −125.3 ppm).

EXAMPLE 2

Example for the Preparation of a Mixture of
4-N,N-dimethylamino-phenylphosphine and
4-(N-methyl-N-ethylamino)-phenylphosphine 62.3 g (0.37 mol) of triethyl phosphite are slowly added dropwise under argon at 160° C. within a period of 90 minutes to a suspension of 50.0 g (0.25 mol) of 4-bromo-N,N-dimethylaniline and 6.5 g (0.05 mol) of nickel chloride, ethyl bromide being given off. The resulting reaction solution is stirred overnight at 160° C., then taken up in toluene and purified over silica gel, the phosphonic acid ester being obtained as intermediate for the title compound in the form of a yellowish oil ($^{31}$P-NMR: 22.32 ppm). For the synthesis of the title compound, 10.0 g (0.039 mol) of that intermediate are slowly added dropwise under argon at −20° C. to a suspension of 2.2 g (0.0584 mol) of lithium aluminium hydride in 250 ml of tetrahydrofuran. After stirring at room temperature overnight there are slowly added dropwise at 0° C. 2.2 g of water, followed by 2.2 g of 10% sodium hydroxide solution and a further 6.6 g of water. The white reaction suspension is filtered with suction under argon and the mother liquor is concentrated using a rotary evaporator. After distillation under a high vacuum (b.p. 157° C./0.004 mbar), the title compound is obtained in the form of a pale yellowish oil ($^{31}$P-NMR: −122.5 ppm).

EXAMPLES 3–6

The compounds of Examples 3 to 6 are prepared analogously to the method described in Example 2 using the respective amine and thio starting materials. The compounds and their physical data are listed in the following Table 1.

TABLE 1

| Example | Phosphine | $^{31}$P-NMR data |
|---|---|---|
| 3 | H$_2$P—⟨phenyl⟩—N(morpholine) | phosphine: −124.6 ppm<br>ester: 21.6 ppm |
| 4 | H$_2$P—⟨phenyl⟩—SCH$_3$ | phosphine: −122.5 ppm<br>ester: 20.11 ppm |
| 5 | H$_2$P—⟨phenyl⟩—N(pyrrolyl) | phosphine: −122.9 ppm<br>ester: 19.2 ppm |
| 6 | H$_2$P—⟨phenyl⟩—N(C$_2$H$_5$)$_2$ | phosphine: −122.5 ppm<br>ester: 21.81 ppm |

Preparation of Bisacylphosphine Oxides

EXAMPLE 7

Example for the Preparation of bis(2,4,6-trimethylbenzoyl)4-[bis(2-methoxyethyl)amino]-phenyl-phosphine oxide 200 ml (0.332 mol; 1.6M) of butyllithium are added dropwise at 0° C., under argon, in the course of 30 minutes to a solution of 33.6 g (0.332 mol) of diisopropylamine in 100 ml of tetrahydrofuran. The resulting solution is added dropwise at −20° C. in the course of 2 hours to a solution of 60.6 g (0.332 mol) of 2,4,6-trimethylbenzoyl chloride and 36.4 g (0.151 mol) of 4-[bis(2-methoxy-ethyl)amino]-phenyl-phosphine (prepared as described in Example 1) in 200 ml of tetrahydrofuran. After 2 hours' stirring, the yellow reaction solution is heated to room temperature and the solvent is removed using a rotary evaporator. The residue is taken up in 200 ml of toluene and washed once with water. 17.1 g (0.151 mol; 30%) of hydrogen peroxide are added to the organic phase. After 2 hours' stirring, washing is carried out first with water, then with saturated sodium hydrogen carbonate solution. Drying is then carried out with magnesium sulfate, followed by filtration and concentration using a rotary evaporator. After crystallisation from isopropanol, 30.2 g (36.4% of theory) of the title compound are obtained in the form of a yellow powder having a melting point of 103–106° C. ($^{31}$P-NMR 10.23 ppm).

$^1$H-NMR (ppm) 7.55–7.62 (t), 7.14–7.21 (t), 6.77 (s), 6.62–6.67 (m), 3.51–3.57 (m), 3.33 (s), 2.23 (s) and 2.15 (s) measured in CDCl$_3$.

EXAMPLES 8–12

The compounds of Examples 8 to 12 are prepared analogously to the method described in Example 7 using the appropriate starting materials. The compounds are shown in the following Table 2.

TABLE 2

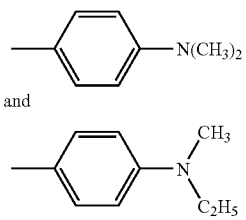

| Ex. | R | Starting materials | NMR data [ppm] measured in CDCl$_3$/melting point [° C.] |
|---|---|---|---|
| 8 | mixture of 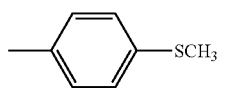 and | 2,4,6-trimethylbenzoyl chloride mixture of 4-dimethylamino-phenylphosphine and 4-(N-methyl-N-ethylamino)-phenyl-phosphine | $^{31}$P-NMR 10.98 $^1$H-NMR 7.57–7.66(m), 6.78(s) 6.61–6.64(m), 3.38–3.45(q), 3.01(s), 2.24(s), 2.17(s) and 1.11–1.16(t)/m.p. 179–180 |
| 9 | 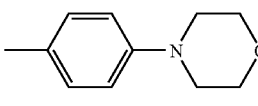 | 2,4,6-trimethylbenzoyl chloride 4-methylthio-phenyl-phosphine | $^{31}$P-NMR 8.02 $^1$H-NMR 7.65–7.71(t), 7.14–7.19(m,), 6.72(s), 2.42(s), 2.18(s) and 2.08(s)/m.p. 93–95 |
| 10 | 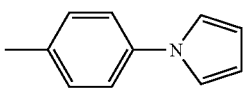 | 2,4,6-trimethylbenzoyl chloride 4-morpholino-phenyl-phosphine | $^{31}$P-NMR 9.62 $^1$H-NMR 7.68–7.74(t), 6.84–6.87(m), 6.79(s), 3.83–3.86(t), 3.25–3.29(t), 2.25(s) and 2.16(s) |
| 11 | 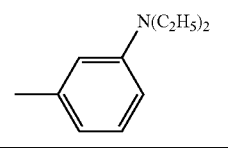 | 2,4,6-trimethylbenzoyl chloride 4-pyrrolo-phenylphosphine | $^{31}$P-NMR 7.41 $^1$H-NMR 7.89–7.95(t), 7.43–7.46(m), 7.15–7.16(t), 6.89(s), 6.38–6.39(t), 2.26(s) and 2.17(s) |
| 12 | N(C$_2$H$_5$)$_2$ (3-substituted phenyl) | 2,4,6-trimethylbenzoyl chloride 3-N,N-diethylamino-phenyl-phosphine | $^{31}$P-NMR 9.89 $^1$H-NMR 8.15–8.18(m), 6.98–7.18(m), 6.72(s), 3.16–3.28(q), 2.17(s), 2.11(s) and 1.02–1.04(t) |

Preparation of Monoacylphosphine Oxides

EXAMPLE 13

Example for the Preparation of 2,4,6-trimethylbenzoyl-benzyl-(4-dimethylamino-phenyl)-phosphine oxide and 2,4,6-trimethylbenzoyl-benzyl-[4-(N-ethyl-N-methyl)amino-phenyl]-phosphine oxide 33 ml (0.0053 mol) of butyllithium 1.6M are slowly added dropwise at –20° C. to 4.5 g (0.0265 mol) of a mixture of 4-dimethylamino-phenylphosphine and 4-(N-ethyl-N-methylamino)phenylphosphine (obtained as described in Example 2) in 100 ml of tetrahydrofuran. With the temperature unchanged, 4.8 g (0.0265 mol) of 2,4,6-trimethylbenzoyl chloride are then added dropwise. After heating to room temperature, 4.5 g (0.0265 mol) of benzyl bromide are added dropwise. After 2 hours' stirring, the orange-brown reaction suspension is concentrated using a rotary evaporator. The residue is taken up in 100 ml of toluene, and 3.0 g (0.0265 mol) of hydrogen peroxide 30% are added. After 2 hours' stirring at from 20 to 30° C., the reaction is complete. The reaction emulsion is poured into water and washed with aqueous saturated sodium hydrogen carbonate solution, then dried over magnesium sulfate and filtered. The mother liquor is concentrated using a rotary evaporator. The residue is purified by means of preparative High Pressure Liquid Chromatography (HPLC) and dried under a high vacuum.

2,4,6-Trimethylbenzoyl-benzyl-(4-dimethyl-amino-phenyl)-phosphine oxide is obtained in the form of a yellow powder having a melting point of 164–166° C. and 2,4,6-trimethylbenzoylbenzyl-(4-N-ethyl-4-N-methyl-amino-phenyl)-phosphine oxide is obtained in the form of a yellow powder having a melting point of 120–123° C.

2,4,6-Trimethylbenzoyl-benzyl-(4-dimethyl-amino-phenyl)-phosphine oxide:

$^{31}$P-NMR 28.11 ppm; $^1$H-NMR (ppm) 7.54–7.61 (t), 7.11–7.30 (m), 6.62–6.68 (m), 3.75–3.84 (t), 3.37–3.47 (t), 2.96 (s), 2.13 (s) and 1.67 (s), measured in CDCl$_3$.

2,4,6-Trimethylbenzoyl-benzyl-(4N-ethyl-4-N-methyl-amino-phenyl)-phosphine oxide:

$^{31}$P-NMR 28.24 ppm; $^1$H-NMR (ppm) 7.31–7.58 (t), 7.10–7.30 (m), 6.61–6.69 (m), 3.76–3.85 (t), 3.28–3.46 (m), 2.89 (s), 2.12 (s) and 1.66 (s), measured in CDCl$_3$.

EXAMPLES 14–16

The compounds of Examples 14 to 16 are obtained analogously to the method described in Example 13 using the appropriate starting materials. The compounds are shown in the following Table 3:

TABLE 3

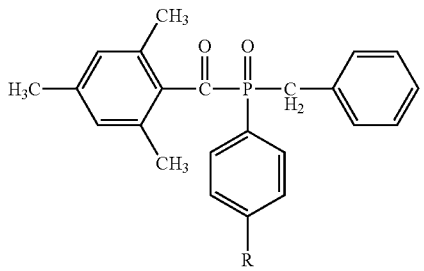

| Ex. | R | Starting materials | NMR data [ppm] measured in CDCl$_3$/m.p.[° C.] |
|---|---|---|---|
| 14 | —N(morpholino) | 4-morpholino-phenylphosphine 2,4,6-trimethylbenzoyl chloride benzyl bromide | $^{31}$P-NMR 27.13 $^1$H-NMR 7.68–7.74(t), 7.18–7.36(m), 6.91–6.94(m), 6.70(s), 3.82–3.91(m), 3.45–3.55(t), 3.26–3.29(t), 2.20(s) and 1.75(s)/m.p. 179–181° C. |
| 15 | —N(pyrrolo) | 4-pyrrolo-phenylphosphine 2,4,6-trimethylbenzoyl chloride benzyl bromide | $^{31}$P-NMR 25.64 $^1$H-NMR 7.89–7.95(t), 7.43–7.46(m), 7.15–7.17(m), 6.90(s), 6.38–6.40(t), 2.26(s) and 2.17(s)/m.p. 60–62° C. |
| 16 | SCH$_3$ | 4-methylthio-phenylphosphine 2,4,6-trimethylbenzoyl chloride benzyl bromide | $^{31}$P-NMR 26.27 $^1$H-NMR 7.69–7.75(m), 7.18–7.37(m), 6.69(s), 3.84–3.89(t), 3.47–3.56(t), 2.49(s), 2.19(s) and 1.74(s)/m.p. 139–142° C. |

EXAMPLE 17

A white printing ink is prepared by mixing
11.5 parts of polyester acrylates (Ebecryl 83, UCB)
5.7 parts of acrylic resin diluted with 40% tripropylene glycol diacrylate (Ebecryl 740/40TP, UCB)
20.0 parts of wetting agent (IRR 331, UCB)
18.5 parts of trimethylolpropane triacrylate (UCB)
11.4 parts of 1,6-hexanediol diacrylate
0.5 parts of flow improver (Modaflow 1990, Solutia Inc.)
2.0 parts of thickener (Aerosil 200)
0.5 part of anti-foam (Byk P-141)
30.0 parts of titanium dioxide.

5 parts of the photoinitiator from Example 10 are added to the resulting mixture. The mixture is applied to an aluminium film and cured under 2×80 W/cm mercury vapour lamps by conveying the sample under the lamps on a belt moving at a constant speed. A fully cured smear-resistant layer is obtained.

EXAMPLE 18

In a composition as described in Example 17, the compound from Example 13 is used as photoinitiator instead of the compound from Example 10. Application and exposure are likewise effected as described in Example 17. A fully cured smear-resistant layer is obtained.

EXAMPLE 19

A secondary optical fiber coating resin (OFC-2 resin) is prepared by mixing the following ingredients:
20 parts of urethane acrylate oligomer (BR 5824, provided by Bomar)
20 parts of ethoxylated bisphenol A diacrylate (EBDA) (SR 601, provided by Sartomer)
32 parts of propoxylated trimethylol propane triacrylate (TMPTA) (SR 492, provided by Sartomer)
25 parts of di-trimethylolpropane tetraacrylate (SR 355, provided by Sartomer)

All components are mixed together with gentle heating to 50° C. to 80° C. for 1 hour, then continued mixing at room temperature for an additional 1 hour. The photoinitiators (Table 4) are added at various wt % concentrations into the OFC-2 resin, the mixture is then heated to 50° C. to 60° C. for 1 hour. In case of the photoinitiator of example 8, the heat is raised to 80° C. and the heating is continued for 4 more hours.

0.05 mm (2 mil, 50 micron) thick films are prepared by applying OFC-2 resin containing photoinitiator to glass plates using a Bird Film applicator, then UV light exposing them under an N$_2$ environment on a Fusion conveyer belt system (Fusion UV model DRS-10/12 conveyer system with nitrogen inerting capability). The lamp is a Fusion VPS/1600 (F600 series) irradiator that is equipped with a "D-lamp" (Fe doped mercury lamp bulb). The belt speed is maintained at 15 m/min (50 ft/min) throughout all operations.

The cured films are analyzed according to a photobleaching test.

The photobleaching is determined from the relative difference in absorption of the long wavelength absorption band (occurring at 380–400 nm). The % photobleaching is defined as:

%ΔOD/OD=−100*(OD−OD$_{initial}$)/OD$_{initial}$, where OD$_{initial}$=OD at 16 mJ/cm$^2$ exposure.

The % ΔOD/OD is found to be an exponentially increasing function of the exposure dose. A linear least squares fit of an exponential function to the data give the characteristic critical dose (beta): % ΔOD/OD=alpha*(1−exp(−Dose/beta))

The photobleaching efficiency is defined by the magnitude of beta (expressed in units of mJ/cm$^2$). Higher photobleaching efficiency is defined by a lower value of beta.

The results are collected in table 4

TABLE 4

| Photoinitiator of example | Beta [mJ/cm$^2$] |
|---|---|
| 8 | 308.6 |
| 16 | 236.5 |
| A | 538.0 |
| B | 315.2 |

Photoinitiator A is bis(2,4,6-trimethylbenzoyl)phenyl phosphine oxide

Photoinitiator B is 2,4,6-trimethylbenzoyl-diphenyl phosphine oxide

The results clearly demonstrate that the compounds according to the present invention exhibit excellent photobleaching properties.

What is claimed is:

1. A compound of formula I

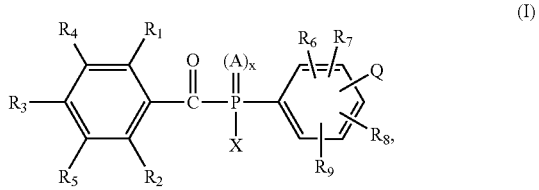

wherein
A is S or O;
x is 0 or 1;
Q is SR$_{10}$ or N(R$_{11}$)(R$_{12}$);
R$_1$ and R$_2$ are each independently of the other C$_1$–C$_{24}$alkyl, OR$_{10}$, CF$_3$ or halogen;
R$_3$, R$_4$ and R$_5$ are each independently of the others hydrogen, C$_1$–C$_{24}$alkyl, OR$_{10}$ or halogen; or two of the radicals R$_1$, R$_2$, R$_3$, R$_4$ and/or R$_5$ together form C$_1$–C$_{20}$alkylene which is uninterrupted or interrupted by O, S or NR$_{13}$;
R$_6$, R$_7$, R$_8$ and R$_9$ are each independently of the others hydrogen, C$_1$–C$_{24}$alkyl; C$_2$–C$_{24}$alkyl which is interrupted one or more times by non-consecutive O atoms and which is unsubstituted or substituted by OH and/or SH; or R$_6$, R$_7$, R$_8$ and R$_9$ are OR$_{10}$; halogen; or phenyl unsubstituted or substituted one or more times by C$_1$–C$_4$alkyl;
R$_{10}$, R$_{11}$ and R$_{12}$ are each independently of the others hydrogen, C$_1$–C$_{24}$alkyl, C$_2$–C$_{24}$alkenyl, C$_3$–C$_8$cycloalkyl, phenyl, benzyl, or C$_2$–C$_{20}$alkyl which is interrupted one or more times by non-consecutive O atoms and which is unsubstituted or substituted by OH and/or SH; or
R$_{11}$ and R$_{12}$ together with the N atom to which they are bonded form a 5- or 6-membered ring, which may also contain O or S atoms or an NR$_{13}$ group;
R$_{13}$ is hydrogen, phenyl, C$_1$–C$_{12}$alkoxy, C$_1$–C$_{12}$alkyl, or C$_2$–C$_{12}$alkyl which is interrupted one or more times by O or S and which is unsubstituted or substituted by OH and/or SH;

X is 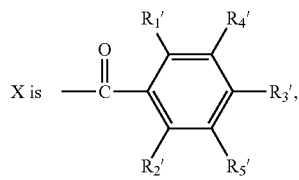

or OR$_{10}$ or X is C$_1$–C$_{24}$alkyl which is unsubstituted or substituted one or more times by OR$_{15}$, SR$_{15}$, N(R$_{16}$)(R$_{17}$), phenyl, halogen, CN, —N=C=A,

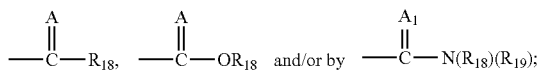

or X is C$_2$–C$_{24}$alkyl which is interrupted one or more times by O, S or NR$_{13}$ and which is unsubstituted or substituted by OR$_{15}$, SR$_{15}$, N(R$_{16}$)(R$_{17}$), phenyl, halogen,

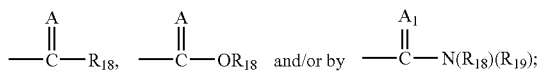

or X is C$_1$–C$_{24}$alkoxy which is uninterrupted or interrupted one or more times by O, S or NR$_{13}$ and which is unsubstituted or substituted one or more times by OR$_{15}$, SR$_{15}$, N(R$_{16}$)(R$_{17}$), phenyl, CN, —N=C=A,

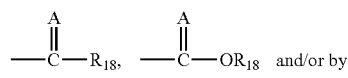

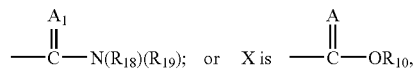

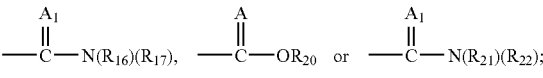

or X is C$_3$–C$_{24}$cycloalkyl unsubstituted or substituted by C$_1$–C$_{20}$alkyl, OR$_{10}$, CF$_3$ or by halogen; or C$_2$–C$_{24}$alkenyl unsubstituted or substituted by C$_6$–C$_{14}$aryl, CN, (CO)OR$_{15}$ or by (CO)N(R$_{18}$)(R$_{19}$);

or X is $C_3$–$C_{24}$cycloalkenyl or is one of the radicals (a) 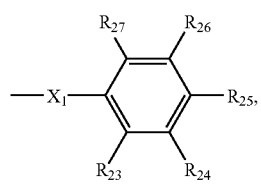

(b) 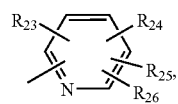

(c) 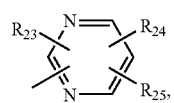

(d) 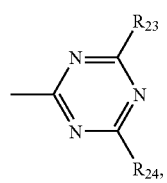

(e) 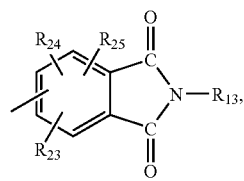

(f) 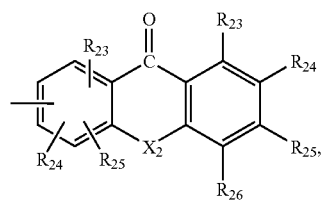

(g) 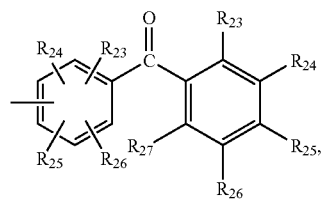

(h) 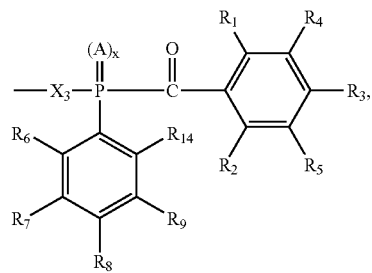

-continued (i) 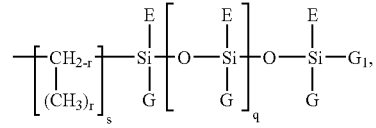

(k) 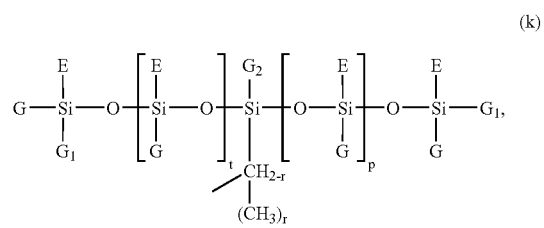

(m) 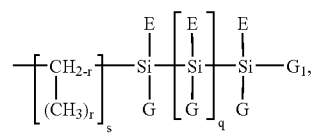

(n) 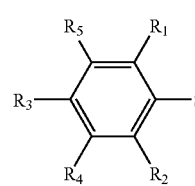

(o) 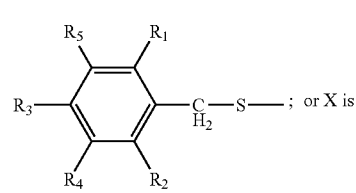; or X is $C_1$–$C_{24}$alkylthio wherein the alkyl radical is uninterrupted or interrupted one or more times by non-consecutive O or S and unsubstituted or substituted by $OR_{15}$, $SR_{15}$ and/or halogen;

$A_1$ is O, S or $NR_{21}$;

$R_{14}$ has one of the meanings given for $R_6$, $R_7$, $R_8$ and $R_9$;

$R_1'$ and $R_2'$ each independently of the other has one of the meanings given for $R_1$ and $R_2$;

$R_3'$, $R_4'$ and $R_5'$ each independently of the others has one of the meanings given for $R_3$, $R_4$ and $R_5$;

$R_{15}$, $R_{16}$ and $R_{17}$ each independently of the others has one of the meanings given for $R_{10}$ or is a radical

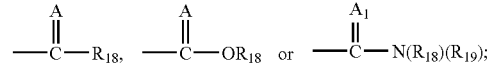

$R_{18}$ and $R_{19}$ are each independently of the other hydrogen, $C_1$–$C_{24}$alkyl, $C_2$–$C_{12}$alkenyl, $C_3$–$C_8$cycloalkyl, phenyl, benzyl; or $C_2$–$C_{20}$alkyl which is interrupted one or more times by O or S and which is unsubstituted or substituted by OH;

$R_{20}$ is $C_1$–$C_{20}$alkyl which is substituted one or more times by $OR_{15}$ or halogen; or is $C_2$–$C_{20}$alkyl which is interrupted one or more times by non-consecutive O atoms and which is unsubstituted or substituted one or more times by $OR_{15}$ or halogen; or $R_{20}$ is $C_2$–$C_{20}$alkenyl or $C_2$–$C_{12}$alkynyl; or $R_{20}$ is $C_3$–$C_{12}$cycloalkenyl which is substituted one or more times by halogen, $NO_2$, $C_1$–$C_6$alkyl, $OR_{10}$ or by $C(O)OR_{18}$; or is $C_7$–$C_{16}$arylalkyl or $C_8$–$C_{16}$arylcycloalkyl;

$R_{21}$ and $R_{22}$ are each independently of the other hydrogen; $C_1$–$C_{20}$alkyl which is substituted one or more times by $OR_{15}$, halogen, styryl, methylstyryl or by —N=C=A; or $C_2$–$C_{20}$alkyl which is interrupted one or more times by non-consecutive O atoms and which is unsubstituted or substituted one or more times by $OR_{15}$, halogen, styryl or by methylstyryl; or $R_{21}$ and $R_{22}$ are each independently of the other $C_2$–$C_{12}$alkenyl; $C_5$–$C_{12}$cycloalkyl which is substituted by —N=C=A or —$CH_2$—N=C=A and may additionally be substituted by one or more $C_1$–$C_4$alkyl substituents; or $R_{21}$ and $R_{22}$ are each independently of the other $C_6$–$C_{14}$aryl unsubstituted or substituted one or more times by halogen, $NO_2$, $C_1$–$C_6$alkyl, $C_2$–$C_4$alkenyl, $OR_{10}$, —N=C=A, —$CH_2$—N=C=A or by $C(O)OR_{18}$; or $R_{21}$ and $R_{22}$ are $C_7$–$C_{16}$arylalkyl; or $R_{21}$ and $R_{22}$ together are $C_8$–$C_{16}$arylcycloalkyl; or $R_{21}$ and $R_{22}$ are each independently of the other

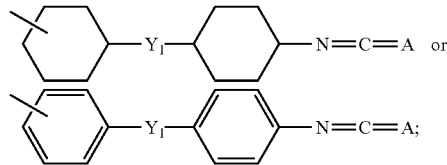

$Y_1$ is O, S, SO, $SO_2$, $CH_2$, $C(CH_3)_2$, $CHCH_3$, $C(CF_3)_2$, (CO) or a direct bond;

$R_{23}$, $R_{24}$, $R_{25}$, $R_{26}$ and $R_{27}$ have one of the meanings given for $R_6$ or are $NO_2$, CN, $SO_2R_{28}$, $OSO_2R_{24}$, $CF_3$, $CCl_3$ or halogen;

$R_{28}$ is $C_1$–$C_{12}$alkyl, halo-substituted $C_1$–$C_{12}$alkyl, phenyl, or phenyl substituted by $OR_{15}$ and/or $SR_{15}$;

$X_1$ is $CH_2$, $CHCH_3$ or $C(CH_3)_2$;

$X_3$ is $C_1$–$C_{24}$alkylene; $C_2$–$C_{24}$alkylene interrupted one or more times by O, S or $NR_{13}$; $C_2$–$C_{24}$alkenylene; $C_2$–$C_{24}$alkenylene interrupted one or more times by O, S or $NR_{13}$; $C_3$–$C_{24}$cycloalkylene; $C_3$–$C_{24}$cycloalkylene interrupted one or more times by O, S or $NR_{13}$; $C_3$–$C_{24}$cycloalkenylene; or $C_3$–$C_{24}$cycloalkenylene interrupted one or more times by O, S or $NR_{13}$; the radicals $C_1$–$C_{24}$alkylene, $C_2$–$C_{24}$alkylene, $C_2$–$C_{24}$alkenylene, $C_3$–$C_{24}$cycloalkylene and $C_3$–$C_{24}$cycloalkenylene being unsubstituted or substituted by $OR_{10}$, $SR_{10}$, $N(R_{11})(R_{12})$ and/or by halogen; or $X_3$ is one of the radicals phenylene,

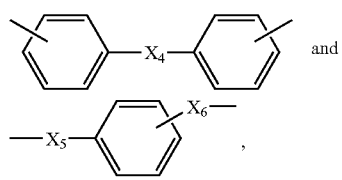

those radicals being unsubstituted or substituted on the aromatic ring by $C_1$–$C_{20}$alkyl; $C_2$–$C_{20}$alkyl which is interrupted one or more times by non-consecutive O atoms and which is unsubstituted or substituted by OH and/or SH; $OR_{10}$, $SR_{10}$, $N(R_{11})(R_{12})$, phenyl, halogen, $NO_2$, CN, (CO)—$OR_{18}$, (CO)—$R_{18}$, (CO)—$N(R_{18})(R_{19})$, $SO_2R_{28}$, $OSO_2R_{28}$, $CF_3$ and/or by $CCl_3$;

or $X_3$ is a group

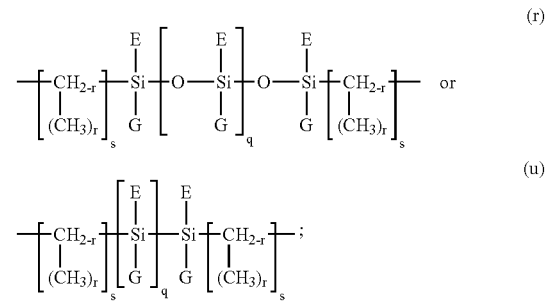

$X_4$ is S, O, $CH_2$, $CHCH_3$, $C(CH_3)_2$, $C(CF_3)_2$, CO, SO or $SO_2$;

$X_5$ and $X_6$ are each independently of the other $CH_2$, $CHCH_3$ or $C(CH_3)_2$;

r is 0, 1 or 2;

s is a number from 1 to 12;

q is a number from 0 to 50;

t and p are each a number from 0 to 20; and

E, G, $G_1$ and $G_2$ are each independently of the others unsubstituted or halo-substituted $C_1$–$C_{12}$alkyl, or phenyl unsubstituted or substituted by one or more $C_1$–$C_4$alkyl substituents.

2. A compound of formula I according to claim 1, wherein

A is O;

x is 1;

Q is $SR_{10}$ or $N(R_{11})(R_{12})$;

$R_1$ and $R_2$ are each independently of the other $C_1$–$C_{12}$alkyl, $OR_{10}$, $CF_3$ or halogen;

$R_3$, $R_4$ and $R_5$ are each independently of the others hydrogen, $C_1$–$C_{12}$alkyl, $OR_{10}$ or halogen;

$R_6$, $R_7$, $R_8$ and $R_9$ are each independently of the others hydrogen, $C_1$–$C_{12}$alkyl, $OR_{10}$, halogen, or phenyl unsubstituted or substituted one or more times by $C_1$–$C_4$alkyl;

$R_{10}$, $R_{11}$ and $R_{12}$ are each independently of the others hydrogen, $C_1$–$C_{12}$alkyl, $C_3$–$C_8$cycloalkyl, $C_2$–$C_{12}$alkenyl, phenyl, benzyl, or $C_2$–$C_{20}$alkyl which is interrupted one or more times by non-consecutive O atoms and which is unsubstituted or substituted by OH and/or SH; or $R_{11}$ and $R_{12}$ together with the N atom to which they are bonded form a 5- or 6-membered ring, which may also contain O atoms or a $NR_{13}$ group;

$R_{13}$ is hydrogen or $C_1$–$C_{12}$alkyl;

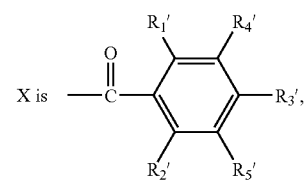

or OR$_{10}$ or X is C$_1$–C$_{24}$alkyl which is unsubstituted or substituted one or more times by OR$_{15}$, SR$_{15}$, N(R$_{16}$)(R$_{17}$), phenyl, halogen, CN,

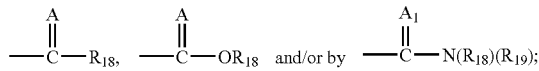

or X is C$_2$–C$_{24}$alkyl which is interrupted one or more times by O, S or NR$_{13}$ and which is unsubstituted or substituted by OR$_{15}$, SR$_{15}$, N(R$_{16}$)(R$_{17}$), phenyl, halogen,

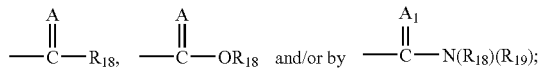

or X is C$_1$–C$_{24}$alkoxy which is uninterrupted or interrupted one or more times by O, S or NR$_{13}$ and which is unsubstituted or substituted one or more times by OR$_{15}$, SR$_{15}$, N(R$_{16}$)(R$_{17}$), phenyl, CN,

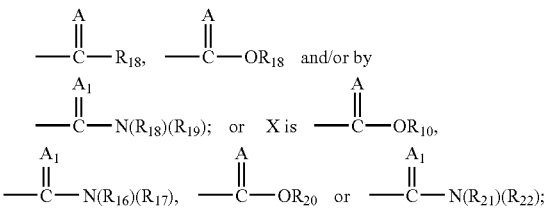

or X is C$_2$–C$_{24}$alkenyl unsubstituted or substituted by C$_6$–C$_{14}$aryl, CN, (CO)OR$_{15}$ or by (CO)N(R$_{18}$)(R$_{19}$);

R$_1$' and R$_2$' each independently of the other has one of the meanings given for R$_1$ and R$_2$; and R$_3$', R$_4$' and R$_5$' each independently of the others has one of the meanings given for R$_3$, R$_4$ and R$_5$;

R$_{14}$ has one of the meanings given for R$_6$, R$_7$, R$_8$ and R$_9$;

R$_{15}$, R$_{16}$ and R$_{17}$ each independently of the others has one of the meanings given for R$_{10}$;

R$_{18}$ and R$_{19}$ are each independently of the other hydrogen, C$_1$–C$_{24}$alkyl, C$_2$–C$_{12}$alkenyl, C$_3$–C$_8$cycloalkyl, phenyl, benzyl; or C$_2$–C$_{20}$alkyl which is interrupted one or more times by O or S;

R$_{20}$ is C$_1$–C$_{20}$alkyl which is substituted one or more times by OR$_{15}$ or halogen; or C$_2$–C$_{20}$alkyl which is interrupted one or more times by non-consecutive O atoms and which is unsubstituted or substituted one or more times by OR$_{15}$ or halogen; or R$_{20}$ is C$_2$–C$_{20}$alkenyl; and R$_{21}$ and R$_{22}$ are each independently of the other hydrogen; C$_1$–C$_{20}$alkyl which is substituted one or more times by OR$_{15}$, halogen, styryl, methylstyryl or by —N═C═A; or C$_2$–C$_{20}$alkyl which is interrupted one or more times by non-consecutive O atoms and which is unsubstituted or substituted one or more times by OR$_{15}$, halogen, styryl or by methylstyryl.

3. A compound of formula I according to claim 1, wherein

A is O;

x is 0 or 1;

Q is SR$_{10}$ or N(R$_{11}$)(R$_{12}$);

R$_1$ and R$_2$ are each independently of the other C$_1$–C$_4$alkyl;

R$_3$, R$_4$ and R$_5$ are each independently of the others hydrogen or C$_1$–C$_4$alkyl;

R$_6$, R$_7$, R$_8$ and R$_9$ are hydrogen;

R$_{10}$, R$_{11}$ and R$_{12}$ are each independently of the others C$_1$–C$_4$alkyl, C$_2$–C$_4$alkenyl, or C$_2$–C$_4$alkyl which is interrupted by non-consecutive O atoms; or R$_{11}$ and R$_{12}$ together with the N atom to which they are bonded form a 5- or 6-membered ring, which may also contain O atoms;

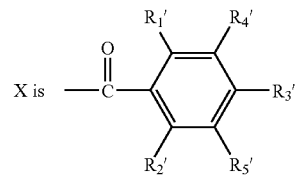

or OR$_{10}$ or X is C$_1$–C$_{12}$alkyl which is unsubstituted or substituted one or more times by OR$_{15}$, phenyl,

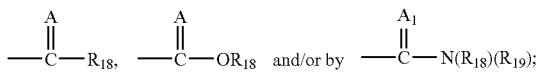

or X is C$_2$–C$_{12}$alkyl which is interrupted one or more times by O and which is unsubstituted or substituted by OR$_{15}$, phenyl,

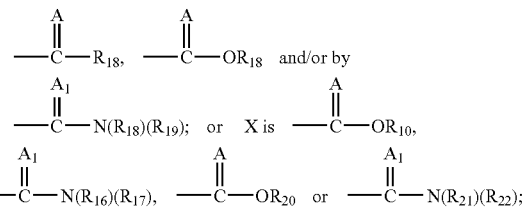

or X is C$_2$–C$_{12}$alkenyl unsubstituted or substituted by C$_6$–C$_{10}$aryl, CN or by (CO)OR$_{15}$;

R$_1$' and R$_2$' each independently of the other has one of the meanings given for R$_1$ and R$_2$;

R$_3$', R$_4$' and R$_5$' each independently of the others has one of the meanings given for R$_3$, R$_4$ and R$_5$;

R$_{15}$, R$_{16}$ and R$_{17}$ each independently of the others has one of the meanings given for R$_{10}$;

R$_{18}$ and R$_{19}$ are each independently of the other hydrogen, C$_1$–C$_4$alkyl, phenyl, benzyl; or C$_2$–C$_6$alkyl which is interrupted one or more times by O;

R$_{20}$ is C$_1$–C$_6$alkyl which is substituted one or more times by OR$_{15}$; or C$_2$–C$_6$alkyl which is interrupted one or more times by non-consecutive O atoms and which is unsubstituted or substituted one or more times by OR$_{15}$; or R$_{20}$ is C$_2$–C$_4$alkenyl; and R$_{21}$ and R$_{22}$ are each independently of the other hydrogen or C$_1$–C$_{20}$alkyl.

4. A compound of formula I according to claim 1 wherein

A is O;

x is 0 or 1;

Q is SR$_{10}$ or N(R$_{11}$)(R$_{12}$);

R$_1$ and R$_2$ are each independently of the other C$_1$–C$_4$alkyl;

R$_3$, R$_4$ and R$_5$ are each independently of the others hydrogen or C$_1$–C$_4$alkyl;

R$_6$, R$_7$, R$_8$ and R$_9$ are hydrogen;

$R_{10}$, $R_{11}$ and $R_{12}$ are each independently of the others $C_1$–$C_4$alkyl, or $C_2$–$C_4$alkyl which is interrupted by non-consecutive O atoms; or $R_{11}$ and $R_{12}$ together with the N atom to which they are bonded form a 5- or 6-membered ring, which may also contain O atoms;

X is 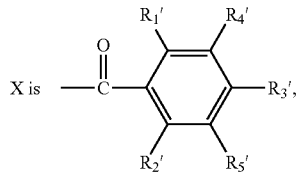

or $C_1$–$C_4$alkyl which is substituted by phenyl;

$R_1'$ and $R_2'$ each independently of the other has one of the meanings given for $R_1$ and $R_2$;

$R_3'$, $R_4'$ and $R_5'$ each independently of the others has one of the meanings given for $R_3$, $R_4$ and $R_5$.

5. A photocurable composition comprising
   (a) at least one ethylenically unsaturated photopolymerisable compound and
   (b) at least one compound of formula I according to claim 1 as photoinitiator.

6. A photocurable composition according to claim 5, comprising in addition to components (a) and (b) further photoinitiators (c) and/or further additives (d).

7. A photocurable composition according to claim 6, comprising as further photoinitiator (c) at least one compound of formula III, IV, V, VI

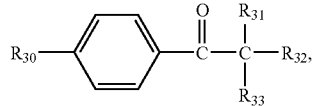 (III)

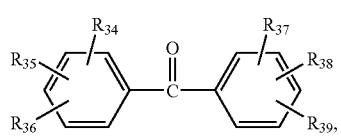 (IV)

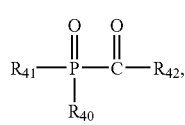 (V)

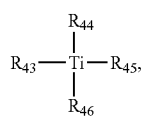 (VI)

wherein
$R_{30}$ is hydrogen, $C_1$–$C_{18}$alkyl, $C_1$–$C_{18}$alkoxy, —OCH$_2$CH$_2$—OR$_{47}$, morpholino, SCH$_3$, a group

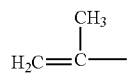

or a group

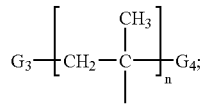

n has a value of from 2 to 10;
$G_3$ and $G_4$ are each independently of the other terminal groups of the polymeric unit, hydrogen or CH$_3$;
$R_{31}$ is hydroxy, $C_1$–$C_{16}$alkoxy, morpholino, dimethylamino or —O(CH$_2$CH$_2$O)$_m$—C$_1$–C$_{16}$alkyl;
$R_{32}$ and $R_{33}$ are each independently of the other hydrogen, $C_1$–$C_6$alkyl, phenyl, benzyl, $C_1$–$C_{16}$alkoxy or —O(CH$_2$CH$_2$O)$_m$—C$_1$–C$_{16}$alkyl, or $R_{32}$ and $R_{33}$ together with the carbon atom to which they are bonded form a cyclohexyl ring;
m is a number from 1 to 20;
wherein $R_{31}$, $R_{32}$ and $R_{33}$ are not all simultaneously $C_1$–$C_{16}$alkoxy or —O(CH$_2$CH$_2$O)$_m$—C$_1$–C$_{16}$alkyl;
$R_{47}$ is hydrogen,

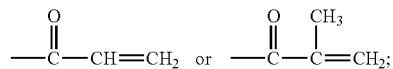

$R_{34}$, $R_{36}$, $R_{37}$ and $R_{38}$ are each independently of the others hydrogen or methyl;
$R_{35}$ and $R_{39}$ are hydrogen, methyl or phenylthio, the phenyl ring of the phenylthio radical being unsubstituted or substituted in the 4-, 2-, 2,4- or 2,4,6-position by $C_1$–$C_4$alkyl;
$R_{40}$ and $R_{41}$ are each independently of the other $C_1$–$C_{20}$alkyl, cyclohexyl, cyclopentyl, phenyl, naphthyl or biphenylyl, those radicals being unsubstituted or substituted by halogen, $C_1$–$C_{12}$alkyl and/or $C_1$–$C_{12}$alkoxy, or $R_{40}$ and $R_{41}$ have a S- or N-containing 5- or 6-membered heterocyclic ring or —(CO)R$_{42}$;
$R_{42}$ is cyclohexyl, cyclopentyl, phenyl, naphthyl or biphenylyl, those radicals being unsubstituted or substituted by halogen, $C_1$–$C_4$alkyl and/or $C_1$–$C_4$alkoxy, or $R_{42}$ is a S- or N-containing 5- or 6-membered heterocyclic ring;
$R_{43}$ and $R_{44}$ are each independently of the other cyclopentadienyl unsubstituted or mono-, di- or tri-substituted by $C_1$–$C_{18}$alkyl, $C_1$–$C_{18}$alkoxy, cyclopentyl, cyclohexyl or halogen;
$R_{45}$ and $R_{46}$ are each independently of the other phenyl which is substituted by fluorine atoms or CF$_3$ in at least one of the two positions ortho to the titanium-carbon bond and may contain, as further substituents at the aromatic ring, polyoxaalkyl or pyrrolinyl unsubstituted or substituted by one or two $C_1$–$C_{12}$alkyl, di($C_1$–$C_{12}$alkyl)aminomethyl, morpholinomethyl, $C_2$–$C_4$alkenyl, methoxymethyl, ethoxymethyl, trimethylsilyl, formyl, methoxy or phenyl substituents, or $R_{45}$ and $R_{46}$ are

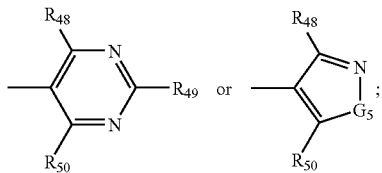

$R_{48}$, $R_{49}$ and $R_{50}$ are each independently of the others hydrogen, halogen, $C_2$–$C_{12}$alkenyl, $C_1$–$C_{12}$alkoxy, $C_2$–$C_{12}$alkoxy interrupted by from one to four O atoms, cyclohexyloxy, cyclopentyloxy, phenoxy, benzyloxy, or phenyl or biphenylyl each unsubstituted or substituted by $C_1$–$C_4$alkoxy, halogen, phenylthio or by $C_1$–$C_4$alkylthio, wherein $R_{48}$ and $R_{50}$ are not both simultaneously hydrogen and in the radical

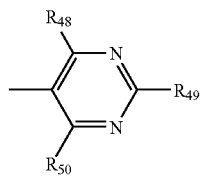

at least one radical $R_{48}$ or $R_{50}$ is $C_1$–$C_{12}$alkoxy, $C_2$–$C_{12}$alkoxy interrupted by from one to four O atoms, cyclohexyloxy, cyclopentyloxy, phenoxy or benzyloxy;

$G_5$ is O, S or $NR_{51}$; and $R_{51}$ is $C_1$–$C_8$alkyl, phenyl or cyclohexyl.

8. A composition according to claim 5 which is a pigmented or non-pigmented surface coating, printing ink, screen-printing ink, offset printing ink, flexographic printing ink, powder coating, printing plate, adhesive, dental compound, bonding compound, glass fiber cable coating, screen-printing stencil, resist material, gel coat or encapsulants for electrical and electronic components.

* * * * *